US012791553B2

(12) United States Patent
Blazeski et al.

(10) Patent No.: US 12,791,553 B2
(45) Date of Patent: Nov. 10, 2026

(54) GRID OF RESPONSES INDICATING DRUG SENSITIVITY

(71) Applicant: The Johns Hopkins University, Baltimore, MD (US)

(72) Inventors: Adriana Blazeski, Baltimore, MD (US); Leslie Tung, Baltimore, MD (US)

(73) Assignee: The Johns Hopkins University, Baltimore, WI (US)

( * ) Notice: Subject to any disclaimer, the term of this patent is extended or adjusted under 35 U.S.C. 154(b) by 993 days.

(21) Appl. No.: 17/599,325

(22) PCT Filed: Mar. 30, 2020

(86) PCT No.: PCT/US2020/025709
§ 371 (c)(1),
(2) Date: Sep. 28, 2021

(87) PCT Pub. No.: WO2020/205732
PCT Pub. Date: Oct. 8, 2020

(65) Prior Publication Data

US 2022/0196636 A1 Jun. 23, 2022

Related U.S. Application Data

(60) Provisional application No. 62/826,030, filed on Mar. 29, 2019.

(51) Int. Cl.
*G01N 33/50* (2006.01)
*C12N 5/077* (2010.01)

(52) U.S. Cl.
CPC ....... *G01N 33/5061* (2013.01); *C12N 5/0657* (2013.01); *G01N 33/5014* (2013.01);
(Continued)

(58) Field of Classification Search
CPC ........... G01N 33/5061; G01N 33/5041; G01N 2800/326; G01N 33/5014; G01N 33/50;
(Continued)

(56) References Cited

U.S. PATENT DOCUMENTS

| | | | |
|---|---|---|---|
| 9,404,140 | B1 | 8/2016 | Molnar et al. |
| 10,183,097 | B2 | 1/2019 | Tung et al. |

(Continued)

OTHER PUBLICATIONS

Blazeski et al. (Engineered heart slices for electrophysiological and contractile studies, Biomaterials. Jul. 2015; 55: 119-128) (Year: 2015) IDS Jan. 26, 2022.*

(Continued)

*Primary Examiner* — Jesse P Frumkin
(74) *Attorney, Agent, or Firm* — Casimir Jones, S.C.; Rikki A. Hullinger

(57) ABSTRACT

Described herein are methods for evaluating a cardiac preparation. The methods involve providing at least one sample comprising one or more cardiac cells, pacing the one or more cardiac cells at two or more fixed rates; and measuring a fixed response of the one or more cardiac cells at each of the two or more fixed rates. Also described herein are methods for evaluating the cardiac effect of a compound. The methods involve providing at least one sample comprising one or more cardiac cells; contacting each sample with the compound; pacing the one or more cardiac cells at two or more fixed rates; and measuring a fixed response of the one or more cardiac cells to the compound at each of the two or more fixed rates.

13 Claims, 27 Drawing Sheets

Specification includes a Sequence Listing.

(52) U.S. Cl.
CPC ..... *G01N 33/5041* (2013.01); *C12N 2503/02* (2013.01); *C12N 2533/90* (2013.01); *G01N 2800/326* (2013.01)

(58) Field of Classification Search
CPC .............. C12N 5/0657; C12N 2503/02; C12N 2533/90; C12N 5/077
See application file for complete search history.

(56) References Cited

U.S. PATENT DOCUMENTS

| | | | | |
|---|---|---|---|---|
| 2017/0173215 | A1* | 6/2017 | Tung | A61L 27/3808 |
| 2017/0204374 | A1 | 7/2017 | Iyoku et al. | |
| 2018/0372724 | A1* | 12/2018 | Khine | G01N 33/48785 |

OTHER PUBLICATIONS

Tandon et al. (Electrical stimulation systems for cardiac tissue engineering, Nat Protoc. 2009; 4(2): 155-173) (Year: 2009).*
International Search Report and Written Opinion for PCT/US2020/025709. Mailed Jul. 1, 2020. 21 pages.
Akhyari et al., The quest for an optimized protocol for whole-heart decellularization: a comparison of three popular and a novel decellularization technique and their diverse effects on crucial extracellular matrix qualities. Tissue Eng Part C Methods. Sep. 2011;17(9):915-26.
Arrowsmith et al., Trial watch: phase II and phase III attrition rates 2011-2012. Nat Rev Drug Discov. Aug. 2013;12(8):569.
Badylak et al., Whole-organ tissue engineering: decellularization and recellularization of three-dimensional matrix scaffolds. Annu Rev Biomed Eng. Aug. 15, 2011;13:27-53.
Baharvand et al., The effect of extracellular matrix on embryonic stem cell-derived cardiomyocytes. J Mol Cell Cardiol. Mar. 2005;38(3):495-503.
Bland et al., Transformations, means, and confidence intervals. BMJ. Apr. 27, 1996;312(7038):1079.
Blazeski et al., Cardiomyocytes derived from human induced pluripotent stem cells as models for normal and diseased cardiac electrophysiology and contractility. Prog Biophys Mol Biol. Oct-Nov. 2012;110(2-3):166-77.
Blazeski et al., Engineered heart slices for electrophysiological and contractile studies. Biomaterials. Jul. 2015;55:119-28.
Blazeski et al., Functional Properties of Engineered Heart Slices Incorporating Human Induced Pluripotent Stem Cell-Derived Cardiomyocytes. Stem Cell Reports. May 14, 2019;12(5):982-995.
Boheler et al., A human pluripotent stem cell surface N-glycoproteome resource reveals markers, extracellular epitopes, and drug targets. Stem Cell Reports. Jun. 6, 2014;3(1):185-203.
Bray et al., Nuclear morphology and deformation in engineered cardiac myocytes and tissues. Biomaterials. Jul. 2010;31(19):5143-50.
Burridge et al., Production of de novo cardiomyocytes: human pluripotent stem cell differentiation and direct reprogramming. Cell Stem Cell. Jan. 6, 2012;10(1):16-28.
Carvalho et al., Characterization of Decellularized Heart Matrices as Biomaterials for Regular and Whole Organ Tissue Engineering and Initial In-vitro Recellularization with Ips Cells. J Tissue Sci Eng. Nov. 28, 2012;Suppl 11:002.
Chartrand. Numerical differentiation of noisy, nonsmooth data. ISRN Appl. Math. 2011, 1-11.
Colan et al., Left ventricular end-systolic wall stress-velocity of fiber shortening relation: a load-independent index of myocardial contractility. J Am Coll Cardiol. Oct. 1984;4(4):715-24.
De Diego et al., Anisotropic conduction block and reentry in neonatal rat ventricular myocyte monolayers. Am J Physiol Heart Circ Physiol. Jan. 2011;300(1):H271-8.
Doss et al., Maximum diastolic potential of human induced pluripotent stem cell-derived cardiomyocytes depends critically on I(Kr). PLoS One. 2012;7(7):e40288. 17 pages.
Duan et al., Hybrid gel composed of native heart matrix and collagen induces cardiac differentiation of human embryonic stem cells without supplemental growth factors. J Cardiovasc Transl Res. Oct. 2011;4(5):605-15.
Durrer et al., Total excitation of the isolated human heart. Circulation. Jun. 1970;41(6):899-912.
Farkas et al., Minimizing repolarization-related proarrhythmic risk in drug development and clinical practice. Drugs. Mar. 26, 2010;70(5):573-603.
Feaster et al., Matrigel Mattress: A Method for the Generation of Single Contracting Human-Induced Pluripotent Stem Cell-Derived Cardiomyocytes. Circ Res. Dec. 4, 2015;117(12):995-1000.
Fermini et al., A New Perspective in the Field of Cardiac Safety Testing through the Comprehensive In Vitro Proarrhythmia Assay Paradigm. J Biomol Screen. Jan. 2016;21(1):1-11.
Fitzgibbon et al., Direct least square fitting of ellipses. IEEE Trans. Pattern Anal. Mach. Intell. 1999; 21, 476-480.
French et al., A naturally derived cardiac extracellular matrix enhances cardiac progenitor cell behavior in vitro. Acta Biomater. Dec. 2012;8(12):4357-64.
Gershlak et al., Mesenchymal stem cells ability to generate traction stress in response to substrate stiffness is modulated by the changing extracellular matrix composition of the heart during development. Biochem Biophys Res Commun. Sep. 20, 2013;439(2):161-6.
Gilchrist et al., High-throughput cardiac safety evaluation and multi-parameter arrhythmia profiling of cardiomyocytes using microelectrode arrays. Toxicol Appl Pharmacol. Oct. 15, 2015;288(2):249-57.
Guyette et al., Bioengineering Human Myocardium on Native Extracellular Matrix. Circ Res. Jan. 8, 2016;118(1):56-72.
Herron et al., Extracellular Matrix-Mediated Maturation of Human Pluripotent Stem Cell-Derived Cardiac Monolayer Structure and Electrophysiological Function. Circ Arrhythm Electrophysiol. Apr. 2016;9(4):e003638. 23 pages.
Kamakura et al., Ultrastructural maturation of human-induced pluripotent stem cell-derived cardiomyocytes in a long-term culture. Circ J. 2013;77(5):1307-14.
Li et al., Cardiotoxicity screening: a review of rapid-throughput in vitro approaches. Arch Toxicol. Aug. 2016;90(8):1803-16.
Liau et al., Pluripotent stem cell-derived cardiac tissue patch with advanced structure and function. Biomaterials. Dec. 2011;32(35):9180-7.
Little et al., Sparse Bayesian step-filtering for high-throughput analysis of molecular machine dynamics. In 2010 IEEE International Conference on Acoustics, Speech and Signal Processing, pp. 4162-4165.
Lu et al., Repopulation of decellularized mouse heart with human induced pluripotent stem cell-derived cardiovascular progenitor cells. Nat Commun. 2013;4:2307.
Lundy et al., Structural and functional maturation of cardiomyocytes derived from human pluripotent stem cells. Stem Cells Dev. Jul. 15, 2013;22(14):1991-2002.
Ma et al., Three-dimensional filamentous human diseased cardiac tissue model. Biomaterials. Feb. 2014;35(5):1367-77.
Ma et al., High purity human-induced pluripotent stem cell-derived cardiomyocytes: electrophysiological properties of action potentials and ionic currents. Am J Physiol Heart Circ Physiol. Nov. 2011;301(5):H2006-17. 14 pages.
Macadangdang et al., Nanopatterned Human iPSC-based Model of a Dystrophin-Null Cardiomyopathie Phenotype. Cell Mol Bioeng. Sep. 2015;8(3):320-332.
Magdy et al., Human Induced Pluripotent Stem Cell (hiPSC)-Derived Cells to Assess Drug Cardiotoxicity: Opportunities and Problems. Annu Rev Pharmacol Toxicol. Jan. 6, 2018;58:83-103.
Mannhardt et al., Human Engineered Heart Tissue: Analysis of Contractile Force. Stem Cell Reports. Jul. 12, 2016;7(1):29-42.
Matsuura et al., Creation of human cardiac cell sheets using pluripotent stem cells. Biochem Biophys Res Commun. Aug. 24, 2012;425(2):321-7.
Mitchell et al., Comparative clinical electrophysiologic effects of diltiazem, verapamil and nifedipine: a review. Am J Cardiol. Feb. 18, 1982;49(3):629-35.

(56) References Cited

OTHER PUBLICATIONS

Nakayama et al., Role of extracellular matrix signaling cues in modulating cell fate commitment for cardiovascular tissue engineering. Adv Healthc Mater. May 2014;3(5):628-41.
Ng et al., Lineage restricted progenitors for the repopulation of decellularized heart. Biomaterials. Oct. 2011;32(30):7571-80.
Nunes et al., Biowire: a platform for maturation of human pluripotent stem cell-derived cardiomyocytes. Nat Methods. Aug. 2013;10(8):781-7.
Oberwallner et al., Human cardiac extracellular matrix supports myocardial lineage commitment of pluripotent stem cells. Eur J Cardiothorac Surg. Mar. 2015;47(3):416-25; discussion 425.
Ott et al., Perfusion-decellularized matrix: using nature's platform to engineer a bioartificial heart. Nat Med. Feb. 2008;14(2):213-21.
Peters et al., Myocardial architecture and ventricular arrhythmogenesis. Circulation. May 5, 1998;97(17):1746-54.
Plissiti et al., Splitting of overlapping nuclei guided by robust combinations of concavity points. In SPIE Medical Imaging 2014, S. Ourselin, and M.A. Styner, eds. p. 903431. 7 pages.
Rao et al., The effect of microgrooved culture substrates on calcium cycling of cardiac myocytes derived from human induced pluripotent stem cells. Biomaterials. Mar. 2013;34(10):2399-411.
Ravens et al., Electrophysiological aspects of changes in heart rate. Basic Res Cardiol. 1998;93 Suppl 1:60-5.
Redfern et al., Relationships between preclinical cardiac electrophysiology, clinical QT interval prolongation and torsade de pointes for a broad range of drugs: evidence for a provisional safety margin in drug development. Cardiovasc Res. Apr. 1, 2003;58(1):32-45.
Rehnelt et al., Frequency-dependent multi-well cardiotoxicity screening enabled by optogenetic stimulation. Int. J. Mol. Sci. 2017: 18, 2634. 19 pages.
Roden. Drug-induced prolongation of the QT interval. Wood, Ed. N Engl J Med. Mar. 4, 2004;350(10):1013-22.
Ronaldson-Bouchard, et al., Advanced maturation of human cardiac tissue grown from pluripotent stem cells. Nature. Apr. 2018;556(7700):239-243.
Spencer et al., Calcium transients closely reflect prolonged action potentials in iPSC models of inherited cardiac arrhythmia. Stem Cell Reports. Aug. 12, 2014;3(2):269-81.
Tester et al., Genetics of long QT syndrome. Methodist Debakey Cardiovasc J. Jan-Mar. 2014;10(1):29-33.
Tzatzalos et al., Engineered heart tissues and induced pluripotent stem cells: Macro- and microstructures for disease modeling, drug screening, and translational studies. Adv Drug Deliv Rev. Jan. 15, 2016;96:234-244.
Veeraraghavan et al., Mechanisms of cardiac conduction: a history of revisions. Am J Physiol Heart Circ Physiol. Mar. 1, 2014;306(5):H619-27.
Wang et al., Modeling the mitochondrial cardiomyopathy of Barth syndrome with induced pluripotent stem cell and heart-on-chip technologies. Nat Med. Jun. 2014;20(6):616-23.
Wang et al., Effect of engineered anisotropy on the susceptibility of human pluripotent stem cell-derived ventricular cardiomyocytes to arrhythmias. Biomaterials. Nov. 2013;34(35):8878-86.
Wang et al., Nitric Oxide-cGMP-PKG Pathway Acts on Orai1 to Inhibit the Hypertrophy of Human Embryonic Stem Cell-Derived Cardiomyocytes. Stem Cells. Oct. 2015;33(10):2973-84.
Wanjare et al., Anisotropic microfibrous scaffolds enhance the organization and function of cardiomyocytes derived from induced pluripotent stem cells. Biomater Sci. Jul. 25, 2017;5(8):1567-1578.
Yue et al., Global endocardial electrical restitution in human right and left ventricles determined by noncontact mapping. J Am Coll Cardiol. Sep. 20, 2005;46(6):1067-75.
Zhang et al., Extracellular matrix promotes highly efficient cardiac differentiation of human pluripotent stem cells: the matrix sandwich method. Circ Res. Oct. 12, 2012;111(9):1125-36.
Zhang et al., Tissue-engineered cardiac patch for advanced functional maturation of human ESC-derived cardiomyocytes. Biomaterials. Jul. 2013;34(23):5813-20.

* cited by examiner

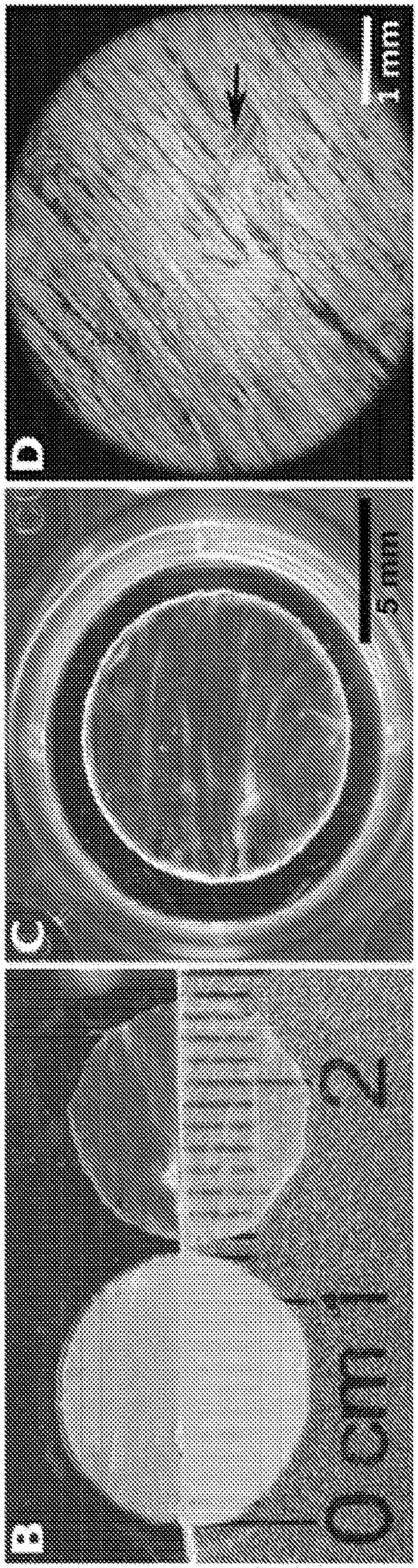
FIG. 1B-D

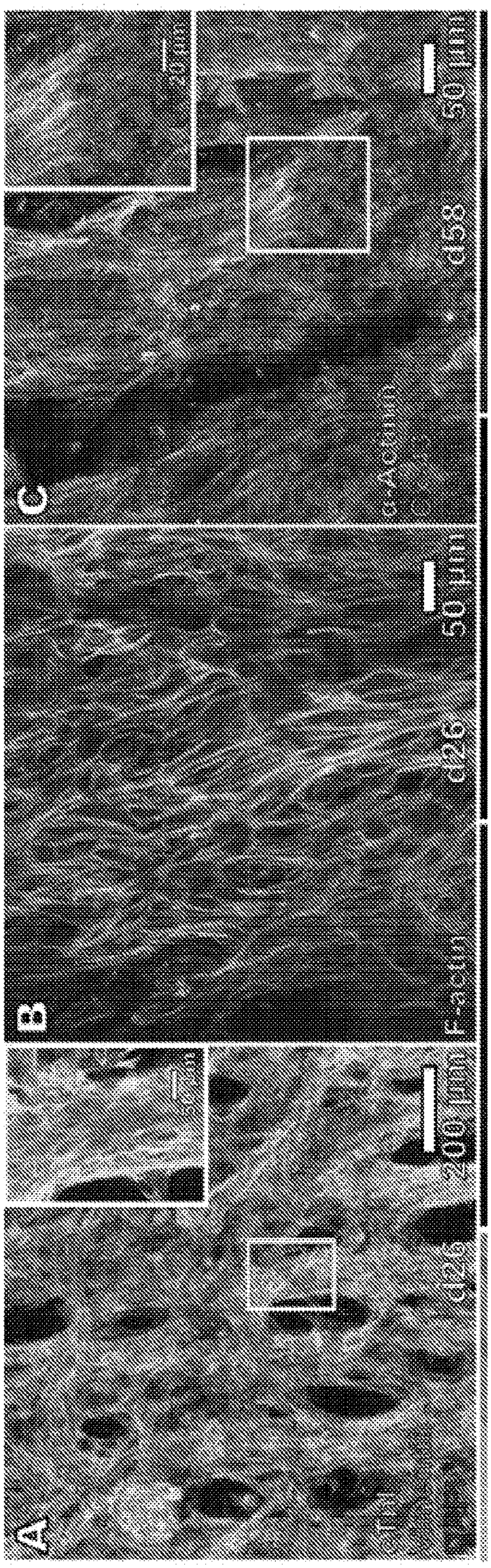
*FIG. 2A-C*

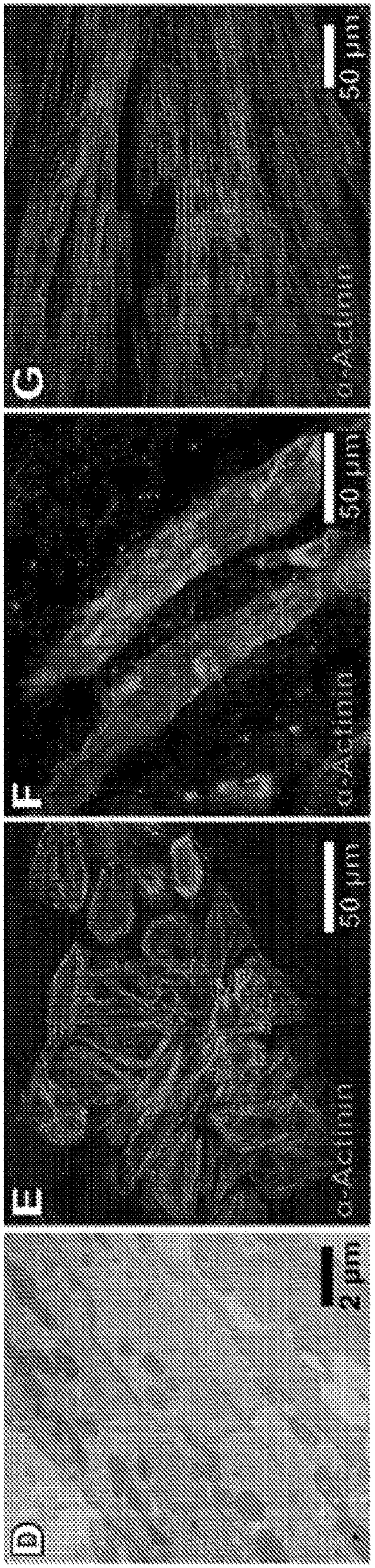
*FIG. 2D-G*

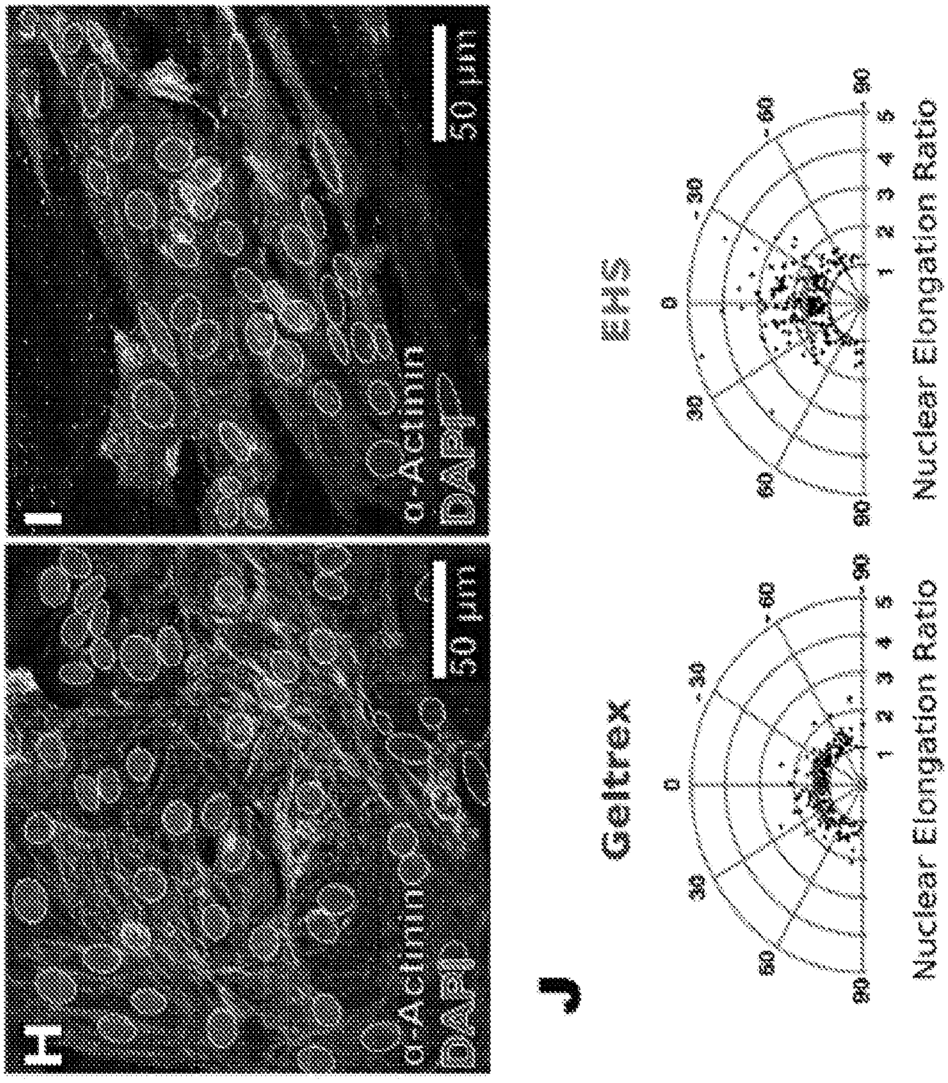
*FIG. 2H-J*

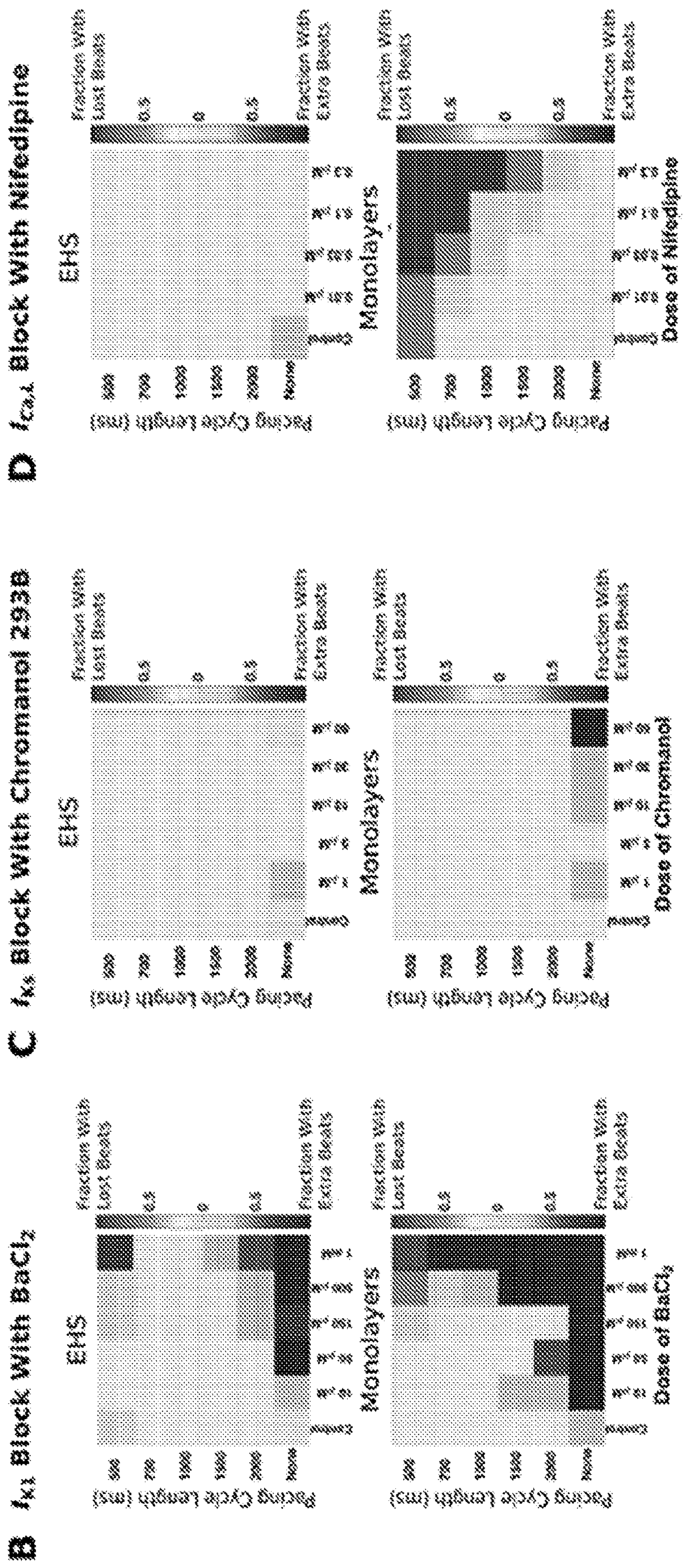
FIG. 6B-D

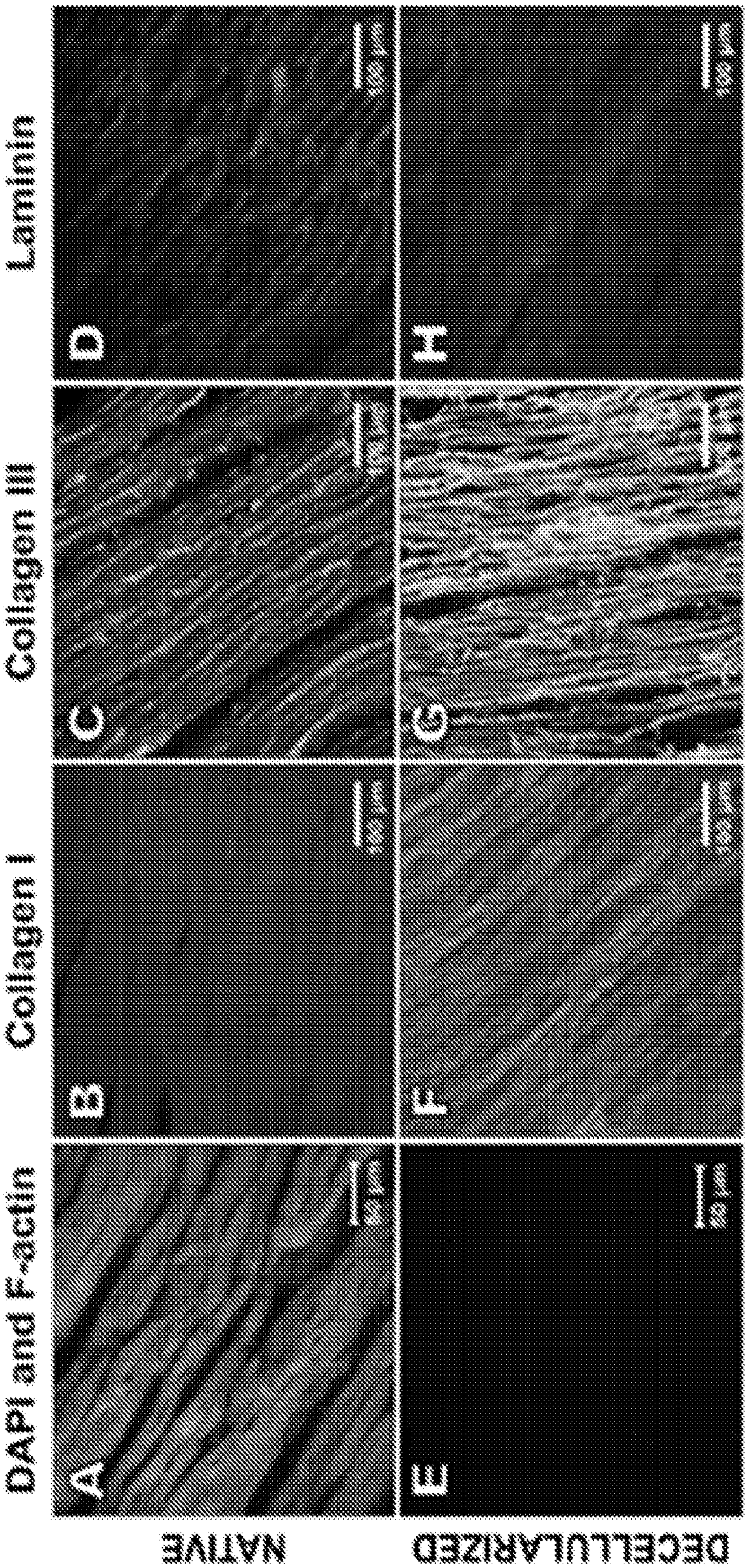
*FIG. 8A-H*

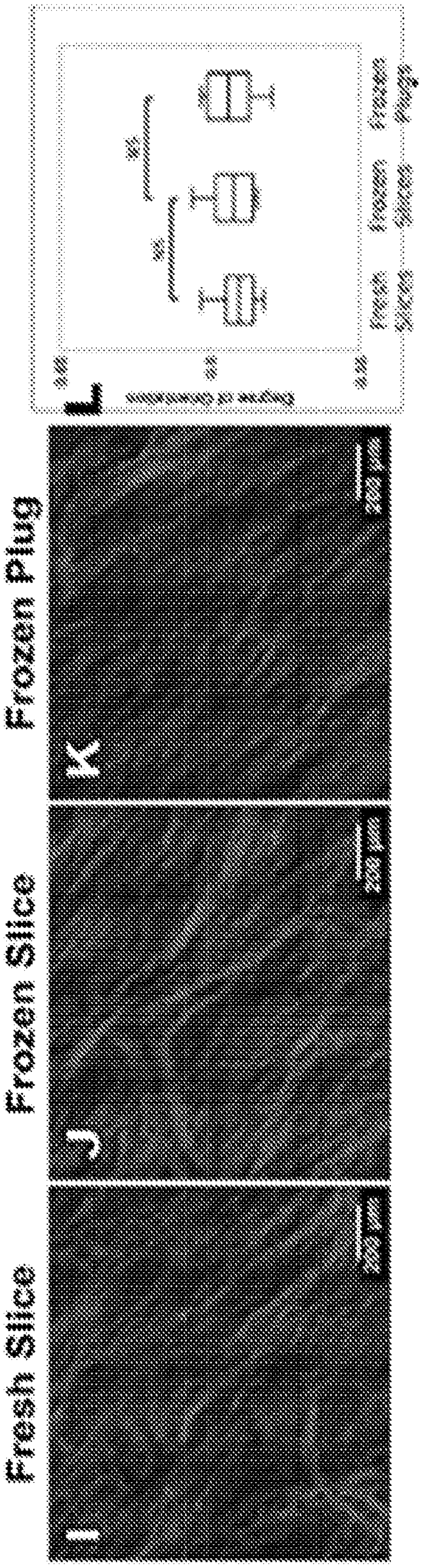
*FIG. 8I-L*

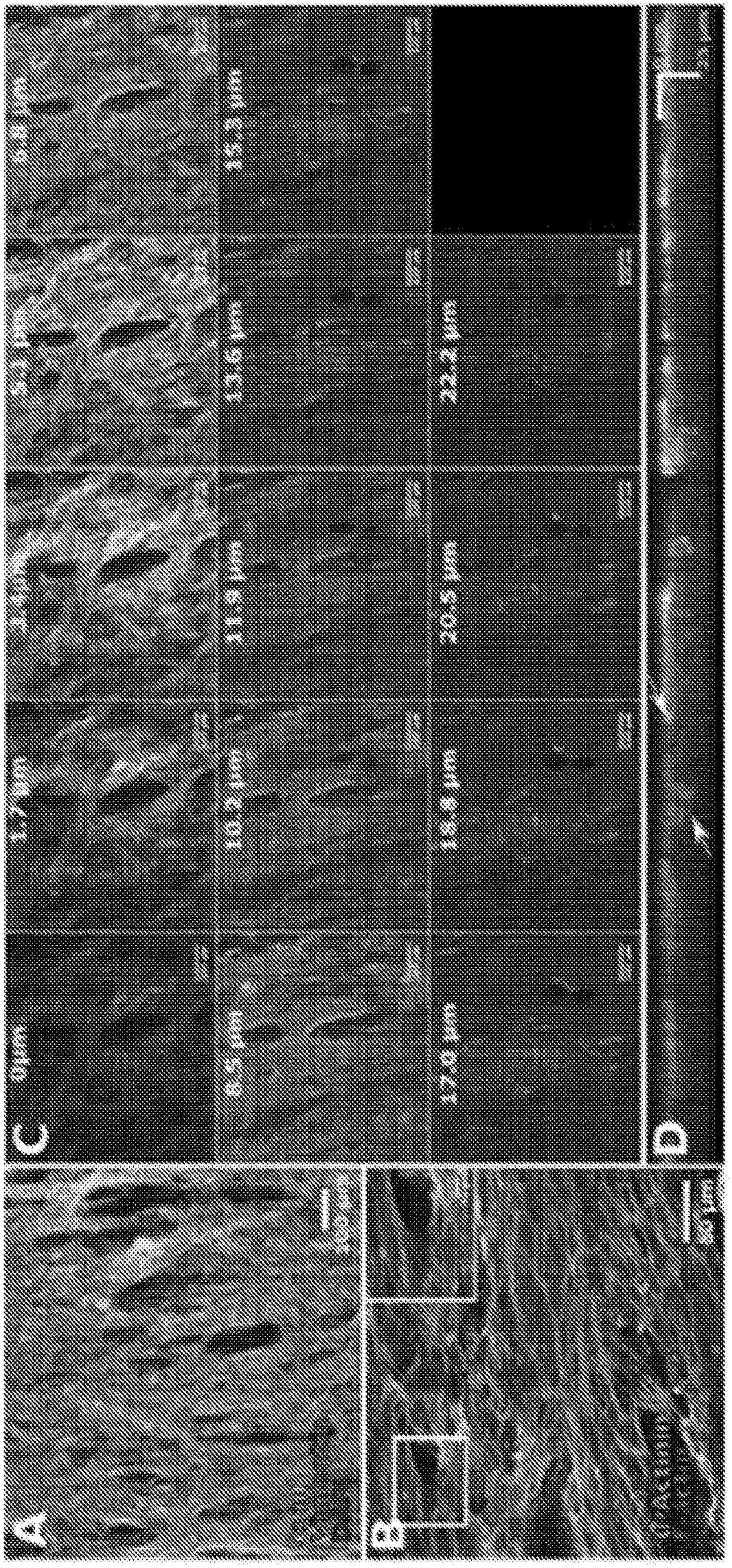
*FIG. 12A-D*

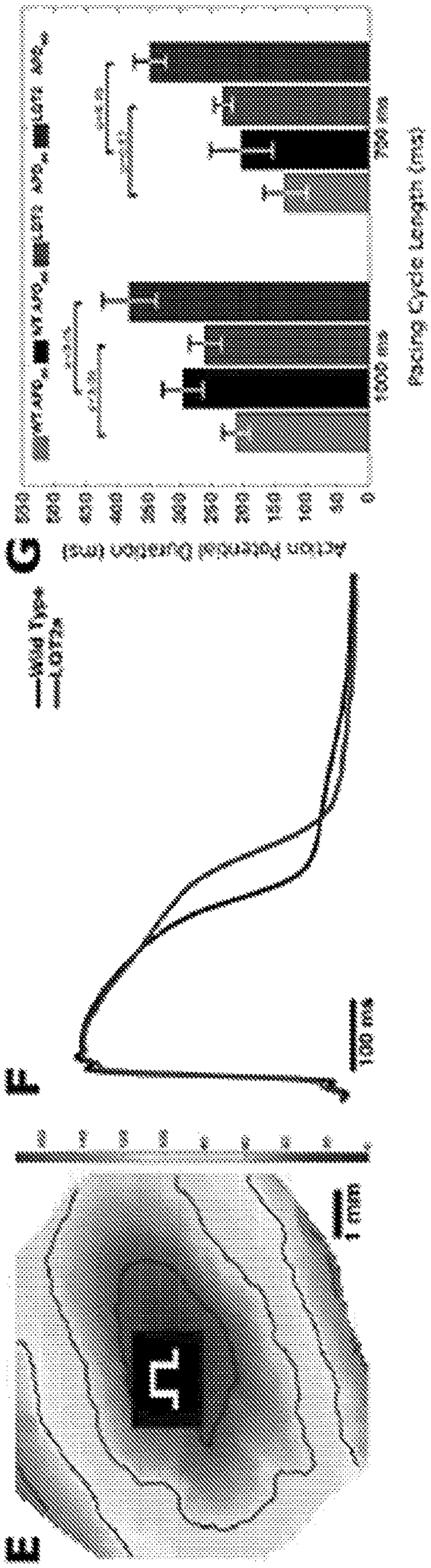
FIG. 12E-G

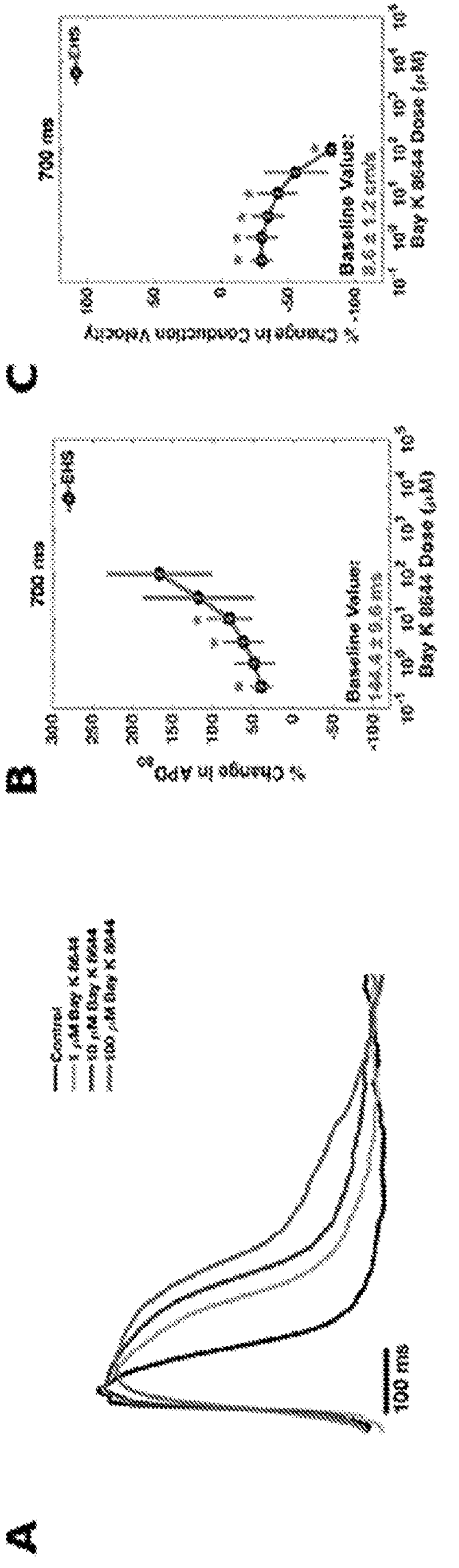
FIG. 14A-C

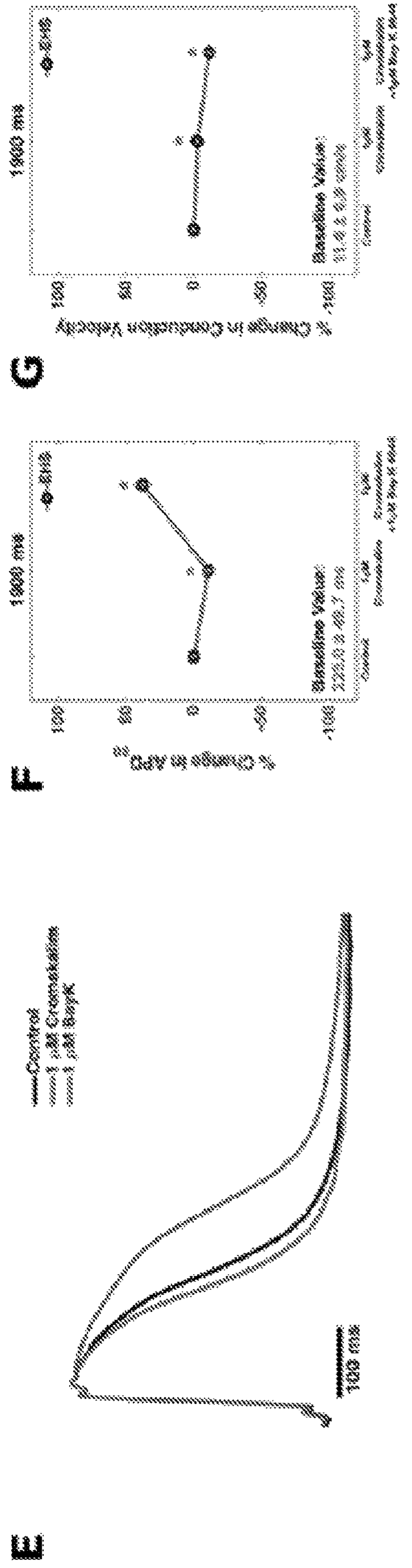
FIG. 14E-G

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
```

cacggcttcc tcgaatcttg 20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
ctgtggagat ggtcgcattg 20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
aggagcgaac ccacaatgtc 20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
aggtggtgcg gaagttgatg 20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
ggtggatgag gagcgatacg 20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
caggctggag ggaagaagtg 20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
ccaactaccg cgcttatgcc 20

<210> SEQ ID NO 8
<211> LENGTH: 20
<212> TYPE: DNA

-continued

```
<213> ORGANISM: Artificial sequence
<220> FEATURE:
<223> OTHER INFORMATION: Synthetic primer

<400> SEQUENCE: 8

ccttctcggt gtcctccttc                                           20
```

GRID OF RESPONSES INDICATING DRUG SENSITIVITY

CROSS-REFERENCE TO RELATED APPLICATIONS

This application claims priority to U.S. Provisional Patent Application No. 62/826,030, filed Mar. 29, 2019, which is incorporated herein by reference in its entirety.

FEDERALLY SPONSORED RESEARCH OR DEVELOPMENT

This invention was made with government support under HL120959 awarded by the National Institutes of Health (NIH). The government has certain rights in the invention.

BACKGROUND

Improvements in methodologies for assessing drug cardiotoxicity during preclinical testing would remove dangerous drugs early on from the pipeline and retain effective drugs, thereby providing cost savings for pharmaceutical companies. The general approach to cardiotoxicity testing has been to evaluate a drug's ability to delay action potential repolarization by measuring its inhibition of hERG channels and the degree to which it causes QT prolongation, a marker for risk of tissue-level arrhythmias. This approach, however, does not capture the biological complexity of cardiac cells and can result in inaccurate assessment of a drug's arrhythmogenic potential. In the last decade, new tools for preclinical cardiac testing have emerged that address this shortcoming by relying on human pluripotent stem cell-derived cardiomyocytes (hPSC-CMs), which represent large numbers of patient-specific cardiac cells. This new field has expanded to include more complex, tissue-like preparations of hPSC-CMs and new tools for functional evaluation of the cells, based on fluorescent reporters, automated patch clamp, and impedance measurements, in an effort to improve drug testing accuracy. Most approaches, however, have been restricted to spontaneous activity of cardiac preparations and fail to control for the rate-dependence of the various ion currents, which can influence the response to drugs.

SUMMARY

In some aspects, described herein is a method for evaluating a sample comprising cardiac cells. The method comprises providing at least one sample comprising one or more cardiac cells; pacing the one or more cardiac cells at two or more fixed rates; and measuring a fixed response of the one or more cardiac cells at each of the two or more fixed rates.

In some aspects, described herein is a method for evaluating the cardiac effect of a compound. The method comprises providing at least one sample comprising one or more cardiac cells; contacting the at least one sample with the compound; pacing the one or more cardiac cells at two or more fixed rates; and measuring a fixed response of the one or more cardiac cells to the compound at each of the two or more fixed rates. In some aspects, a plurality of samples is provided, wherein each of the samples comprises at least one cardiac cell.

In some aspects, the method further comprises measuring a spontaneous response of the one or more cardiac cells to the compound prior to pacing the one or more cardiac cells at the two or more fixed rates. In certain aspects, the two or more fixed rates have a range from about 0.5 Hz to about 2 Hz.

Measuring the spontaneous response and/or fixed response of the one or more cardiac cells may comprise measuring one or more of pace-capture, repolarization time, contraction strength, and conduction velocity. In some aspects, the method further comprises reporting the measured spontaneous response and/or fixed response of the one or more cardiac cells on a binary classification scale. The reported spontaneous response and/or fixed response of each cardiac cell may be compiled into a single visual representation. In some aspects, the visual representation is color coded.

In certain aspects, the sample comprises a single cell, a cell monolayer, a cell cluster, engineered cardiac tissue, cardiac organoid, cardiac tissue explant, or whole heart.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1A:
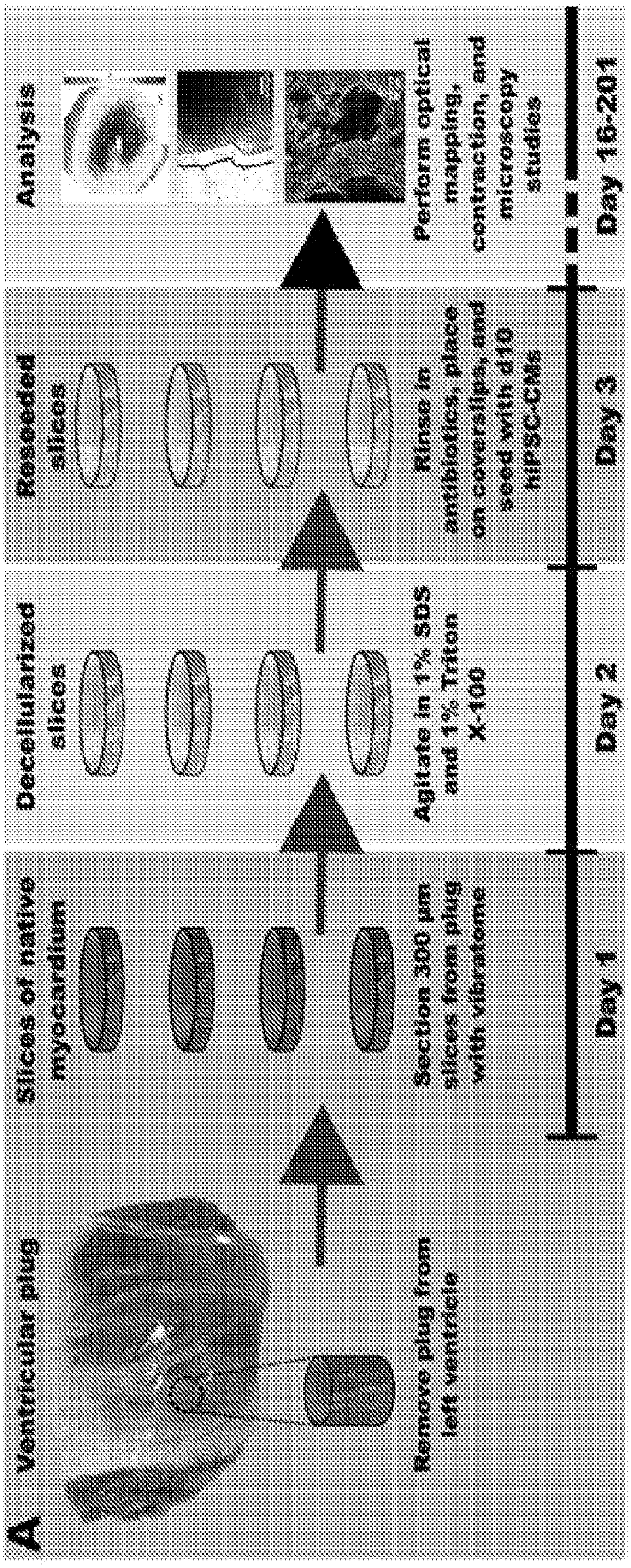
Figure 3:
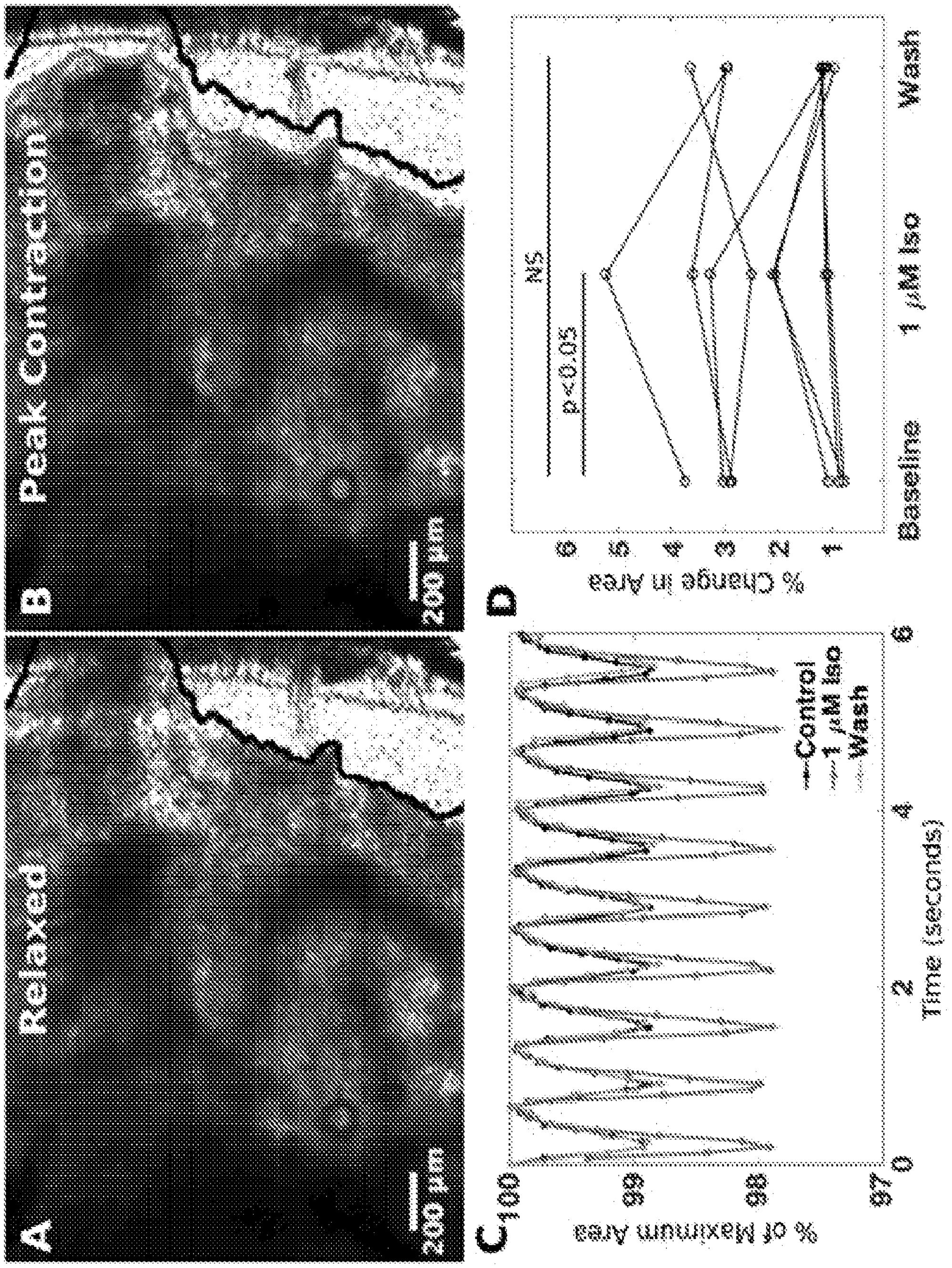
Figure 4:
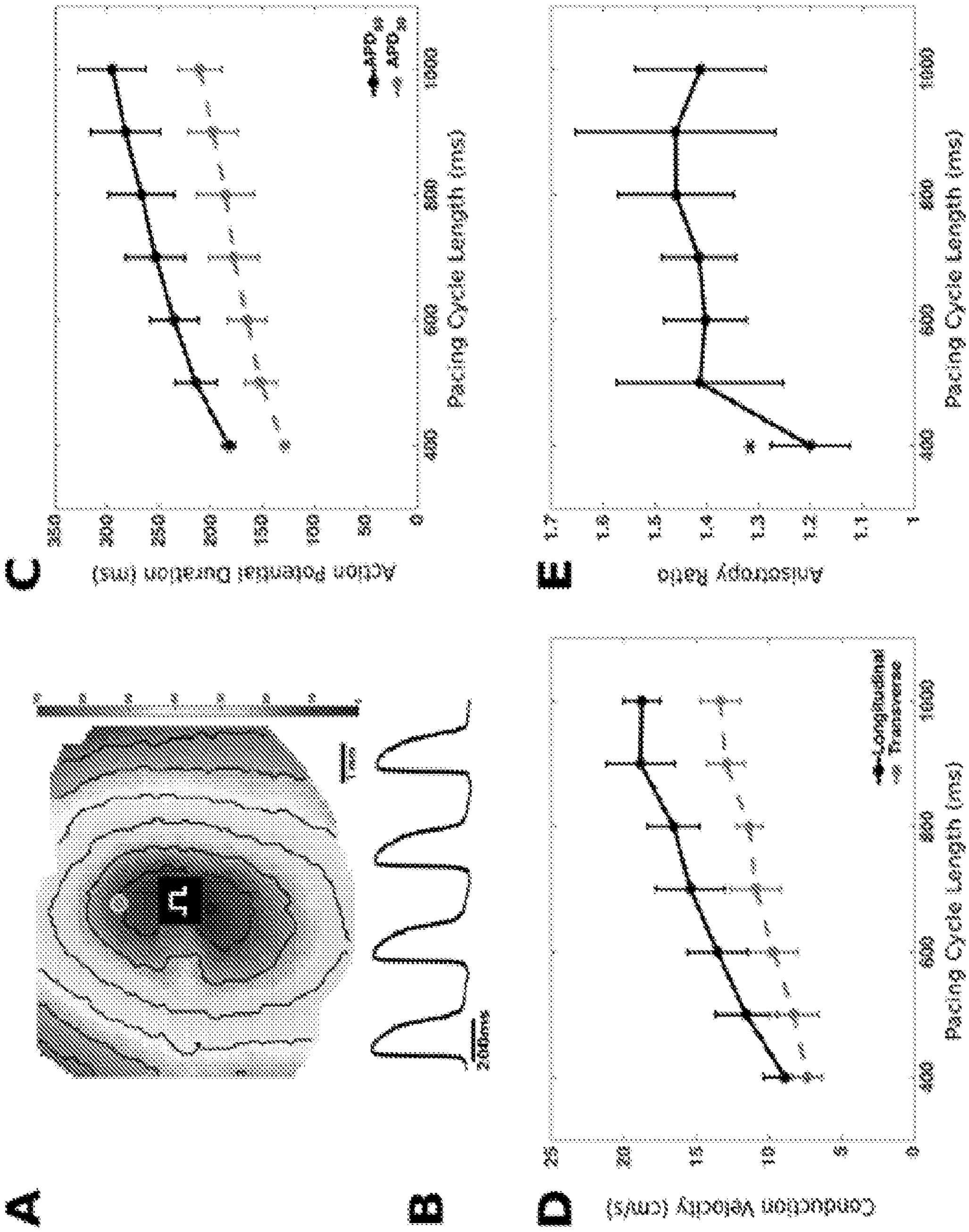
Figure 5:
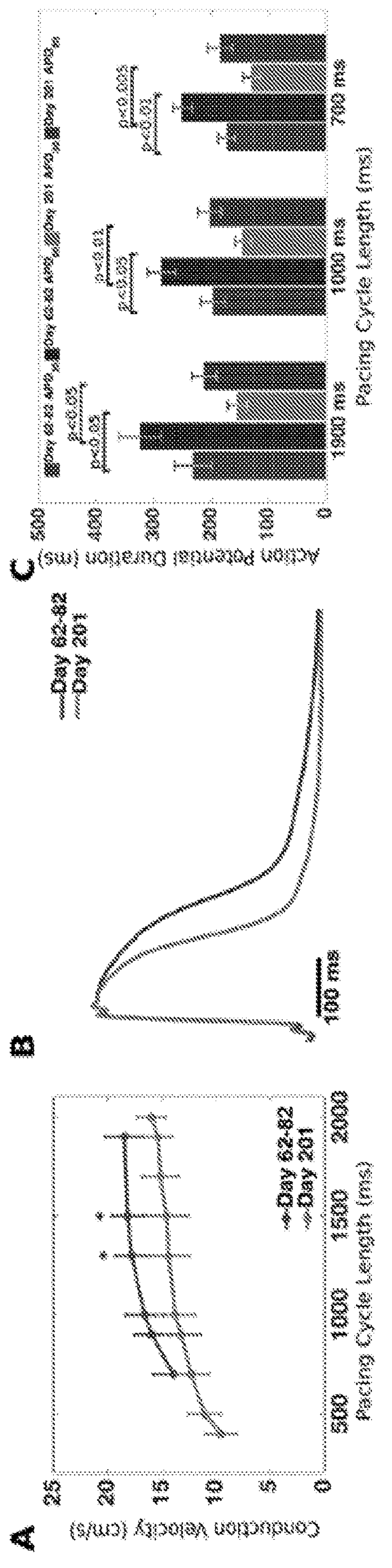
Figure 11:
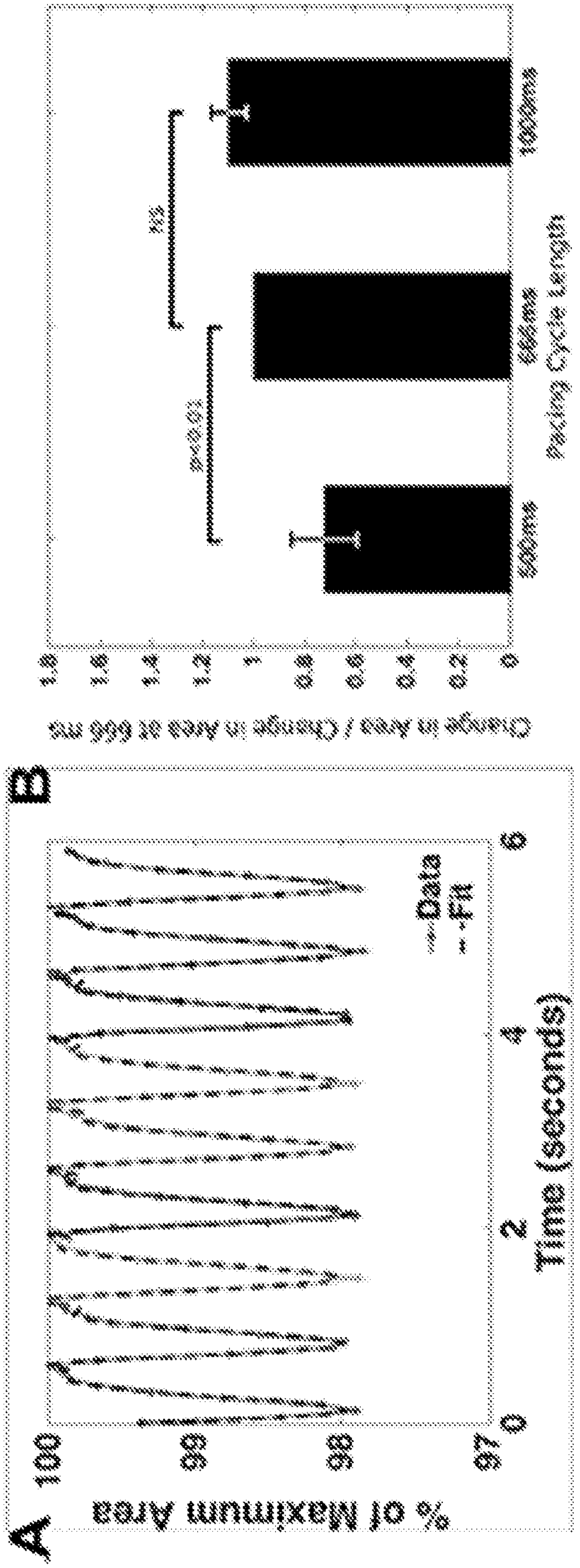
Figure 13:
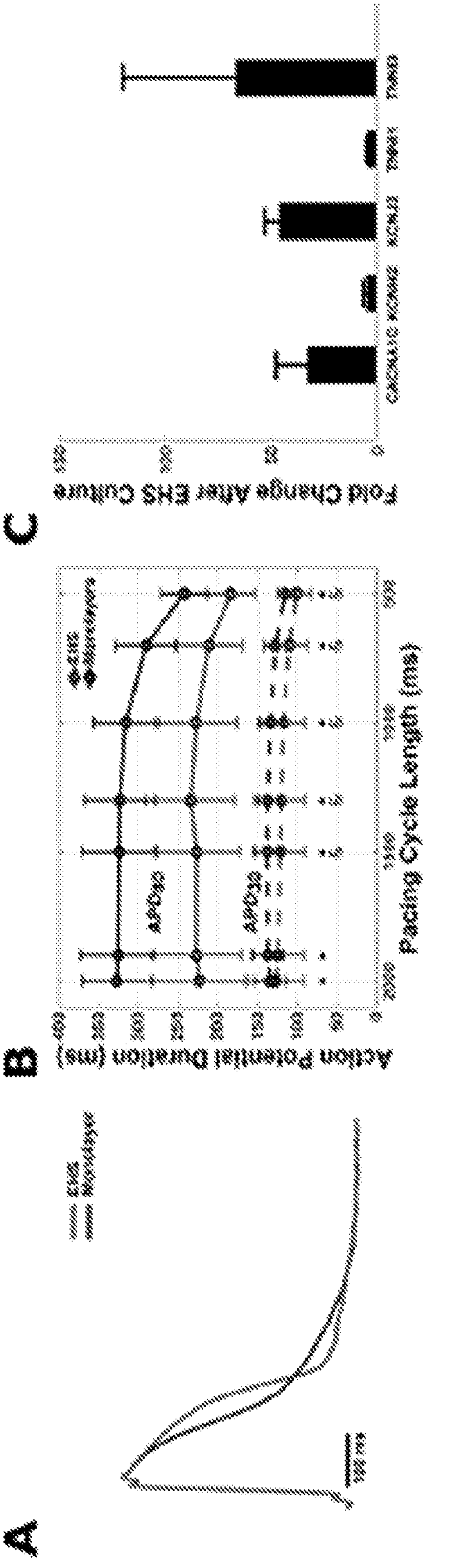
Figure 14D:
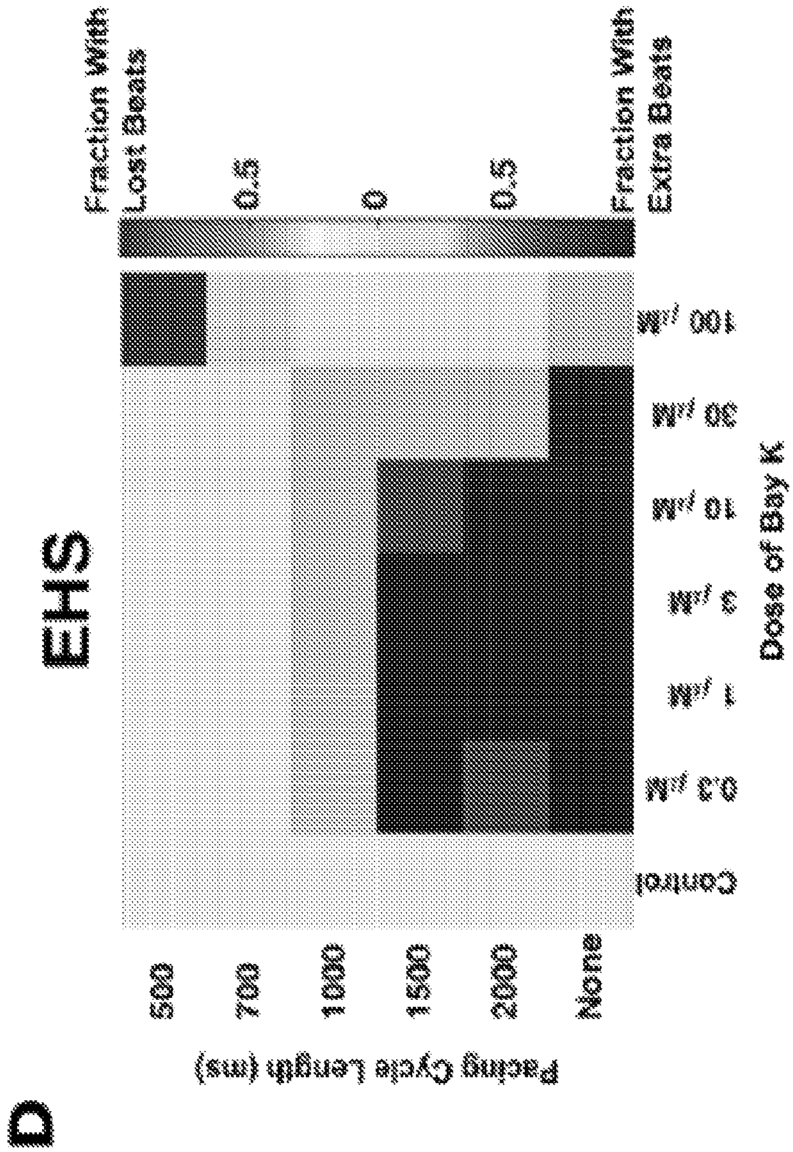
Figure 15:
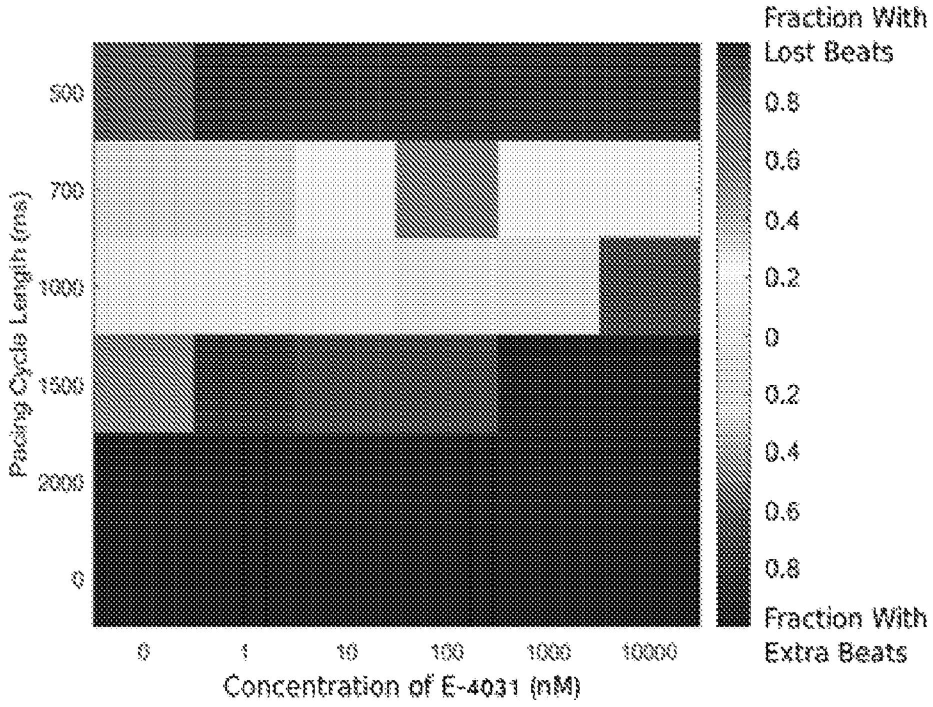

Having thus described the presently disclosed subject matter in general terms, reference will now be made to the accompanying Figures, which are not necessarily drawn to scale, and wherein:

FIG. 1A, FIG. 1B, FIG. 1C, and FIG. 1D demonstrate the preparation of EHS. (FIG. 1A) The workflow for preparing slices. (FIG. 1B) Slices of myocardium before (left) and after decellularization (right). (FIG. 1C) Slices attached to the edges of a plastic coverslip and placed in the wells of a standard culture dish prior to cell seeding. (FIG. 1D) Light micrograph of decellularized slice showing ECM and portion of vasculature (arrow indicates vessel). See also FIG. 8;

FIG. 2A, FIG. 2B, FIG. 2C, FIG. 2D, FIG. 2E, FIG. 2F, FIG. 2G, FIG. 2H, FIG. 2I, and FIG. 2J illustrate the morphology of hiPSC-CMs on EHS. (FIG. 2A) Immunostaining for cardiac troponin I (green), DAPI (blue) and vimentin (magenta) in EHS (inset scale bar=50 μm). (FIG. 2B) Staining for F-actin in EHS. (FIG. 2C) Staining for α-actinin (green) and Cx43 (red) in EHS (inset scale bar=20 μm). Higher magnification view in the insets correspond to region outlined by white rectangle. hiPSC-CMs were cultured in EHS for either 16 days or 48 days (d26 or d58 of differentiation, respectively). (FIG. 2D) Transmission electron micrograph of hiPSC-CMs in EHS showing myofilaments and mitochondria. (FIG. 2E) Staining for α-actinin in hiPSC-CMs cultured at a low density on Geltrex or (FIG. 2F) on decellularized slices. (FIG. 2G) Staining for α-actinin in hiPSC-CMs seeded on slices at d13, dissociated after prolonged culture (139 days) and replated on Geltrex. (FIG. 2H) DAPI staining of nuclei (blue, delineated by white outline) in hiPSC-CMs (green, α-actinin immunostaining) on Geltrex and (FIG. 2I) on EHS. (FIG. 2J) Analysis of d24 hiPSC-CM nuclear shape and orientation in EHS and on Geltrex. Radial distances of data points reflect elongation ratios (long axis/short axis) of nuclei that were fitted by white ellipses in (FIG. 2H) and (FIG. 2I). Solid blue and red lines indicate mean nuclear elongation ratios for cells on Geltrex or in EHS, respectively, while arc lengths correspond to standard deviation from the mean angle of orientation. See also FIG. 9 and FIG. 10;

FIG. 3A, FIG. 3B, FIG. 3C, and FIG. 3D demonstrate contraction of EHS and response to isoproterenol. (FIG. 3A) EHS in relaxed state and (FIG. 3B) at peak contraction (shortening) in response to 666-ms pacing. Black line in (FIG. 3A, FIG. 3B) delineates edge of EHS when fully relaxed and red line (FIG. 3B) delineates edge of EHS at maximum contraction. (FIG. 3C) Percent change in area during contraction (contraction amplitude) in response to pacing at 666 ms normalized to area at rest, plotted at baseline, after the addition of 1 μM isoproterenol, and after washout of the drug. (FIG. 3D) Percent change in EHS area during isoproterenol and after washout (n=8 for each group). NS indicates mean is not significantly different from control values. See also FIG. 11;

FIG. 4A, FIG. 4B, FIG. 4C, FIG. 4D, and FIG. 4E show the optical mapping of EHS. (FIG. 4A) A sample activation map of EHS paced at 500 ms cycle length. Black lines indicate isochrones at 10 ms intervals. Rectangular symbol indicates pacing site. (FIG. 4B) Sample voltage trace is shown from the site indicated by the magenta point in (FIG. 4A). (FIG. 4C) APD30 and APD80 as function of pacing cycle length (PCL), (FIG. 4D) CVs in the longitudinal and transverse directions, and (FIG. 4E) anisotropy ratios at different pacing rates for d54-58 EHS (n=4 for PCL=400 ms, and n=6 for PCL>400 ms). * indicates $p<0.05$ for difference compared with anisotropy ratio at PCL=1000 ms. Error bars denote standard deviation. See also Table 1, FIG. 12;

FIG. 5A, FIG. 5B, and FIG. 5C show optical mapping of EHS after prolonged culture. (FIG. 5A) CVs plotted for day 62-82 EHS and day 201 EHS (* indicates $p<0.05$ for comparisons between day 62-82 and day 201 at each PCL). (FIG. 5B) Sample AP traces at 1000 ms PCL in younger and older EHS. (FIG. 5C) APD30 and APD80 values at 1900 ms, 1000 ms, and 700 ms PCL for day 62-82 and day 201 EHS. Error bars denote standard deviation. n=3 for day 62-82 EHS, and n=5 for day 201 EHS. See also Table 2;

FIG. 6A, FIG. 6B, FIG. 6C, and FIG. 6D demonstrate the effect of cardioactive drugs on paced beats. (FIG. 6A) GRIDS maps of EHS and monolayer responses to E-4031. Sample traces of optical recordings from EHS (right, i-v, top black traces) and corresponding pacing stimuli (right, i-v, bottom blue traces) for examples of: (i) spontaneous activity, (ii) spontaneous activity when no pacing stimuli were applied, (iii) extra beats during pacing, (iv) capture of each paced beat, and (v) lost beats during pacing. PCL and dose of E-4031 applied during the sample traces is indicated by the squares labelled i-v in the color grid (left). Color bars indicate the fraction of total monolayers or EHS which lost beats (illustrated in FIG. 6A, v) or extra beats (illustrated in FIG. 6A, iii). n=5-10 for monolayers, and n=5-18 for EHS. (FIG. 6B) GRIDS maps for BaCl2. n=3 for monolayers and n=3-6 for EHS. (FIG. 6C) GRIDS maps for chromanol 293B. n=3 for monolayers and n=3-6 for EHS. (FIG. 6D) GRIDS maps for nifedipine. n=3 each for monolayers and EHS. See also FIG. 11 and FIG. 14;

FIG. 7A, FIG. 7B, FIG. 7C, and FIG. 7D demonstrate the effect of cardioactive drugs on action potentials and conduction velocities. Action potential recordings from EHS (i) and monolayers (ii) for increasing doses of (FIG. 7A) E-4031, (FIG. 7B) $BaCl_2$, (FIG. 7C) chromanol 293B), and (FIG. 7D) nifedipine. Changes in APD80 (FIG. 7A-FIG. 7C, iii), APD30 (FIG. 7D, iii) and CV (FIG. 7A-FIG. 7D, iv) are plotted for each drug. EHS and monolayers were paced at 1500 ms cycle length for E-4031 and nifedipine and at 1000 ms cycle length for $BaCl_2$ and chromanol 293B. Baseline values of APD and CV before the application of drug are indicated in red for EHS and blue for monolayers in (iii) and (iv) for each drug. Error bars denote standard deviation. Red * indicates $p<0.05$ when comparing the percent change for EHS to 0. Blue * indicates $p<0.05$ when comparing the percent change for monolayers to 0. # indicates $p<0.05$ when comparing baseline values for EHS to baseline values for monolayers. n values for EHS and monolayers exposed to each drug are the same as in FIG. 6. See also FIG. 14;

FIG. 8A, FIG. 8B, FIG. 8C, FIG. 8D, FIG. 8E, FIG. 8F, FIG. 8G, FIG. 8H, FIG. 8I, FIG. 8J, FIG. 8K, and FIG. 8L show the characterization of dECM slices and is related to FIG. 1. Immunostaining of slices for F-actin (green) and DAPI (blue) indicates the presence of (FIG. 8A) cellular content before but (FIG. 8E) not after decellularization. The extracellular matrix components for (FIG. 8B, FIG. 8F) collagen I, (FIG. 8C, FIG. 8G) collagen III, and (FIG. 8D, FIG. 8H) laminin in the slice both before (top row) and after (bottom row) decellularization. Second harmonic generation imaging showing the collagen fibers in (FIG. 8I) a slice sectioned and decellularized from a fresh porcine heart, (FIG. 8J) a slice sectioned from a porcine heart frozen for >48 hours at −80° C. and subsequently decellularized, and (FIG. 8K) a slice originating from a plug frozen for >48 hours at −80° C. and subsequently sectioned and decellularized. (FIG. 8L) The degree of orientation of the collagen fibers was similar in all three groups, n=8 for each group. NS indicates means are not significantly different;

FIG. 9A, FIG. 9B, and FIG. 9C show the characterization of cell populations and is related to FIG. 2. Cardiomyocytes were analyzed via flow cytometry at several stages: on day 17 (d17) after initiating cardiomyocyte differentiation according to (FIG. 9A) standard protocols, (FIG. 9B) after re-plating into 2D tissue culture plates at d17 and long-term maintenance in culture for an additional 61 days, and (FIG. 9C) after replating onto dECM slices at d17 to form EHS and maintained in culture for an additional 61 days. Data shows percentage of non-cardiomyocytes (cTnT−, blue) cell and percentage of cardiomyocytes (cTnT+, red) in each panel. Histogram counts were extracted by gating on unstained cells and cells stained only with a secondary antibody control (to remove autofluorescence and background nonspecific secondary staining);

FIG. 10A, FIG. 10B, and FIG. 10C show the morphology of hiPSC-CMs on EHS and is related to FIG. 2. EHS seeded with hiPSCCMs had multiple layers of cells, with (FIG. 10A, FIG. 10C) CMs in contact with the ECM of the slice exhibiting greater alignment than (FIG. 10B, FIG. 10D) CMs in a second layer sitting on top of the first CM layer, farther from the slice and forming the surface of the EHS. (FIG. 10D) EHS also exhibited localization of Cx43 around the perimeters of the cells (white arrows). Top row images are from d26 EHS and bottom row images are from d69 EHS;

FIG. 11 and FIG. 11B demonstrate the contraction of EHS in response to different pacing rates and is related to FIG. 1. (FIG. 11A) Contraction traces of EHS exposed to 1 μM isoproterenol plotted in FIG. 1C. Each cycle of contraction and relaxation was fit by a polynomial of degree 5 using a least squares fitting method. The data for each cycle are plotted in a different color, and the fitted curve for that cycle plotted on top using a dashed black line. The difference in the minimum (representing maximum EHS contraction during one cycle) calculated by the presently disclosed data compared to that calculated by the best fit line was 0.02±0.01% for the control, 0.06±0.04% for the isoproterenol, and 0.05±0.03% for the washout traces plotted in FIG. 1C. (FIG. 11B) Contraction amplitudes at 500 ms and 1000 ms pacing rates were normalized by the contraction amplitudes at a pacing rate of 666 ms. Error bars denote standard deviation. NS indicates mean is not significantly different from 1. n=6 for each group;

FIG. 12A, FIG. 12B, FIG. 12C, FIG. 12D, FIG. 12E, FIG. 12F, and FIG. 12G show that EHS comprised of LQT2 hiPSC-CMs and is related to FIG. 2. EHS were seeded with LQT2 hiPSC-CMs 10 days after the start of differentiation and maintained in culture for 13 days before evaluation (at d23). (FIG. 12A) Immunostaining for cardiac troponin I (green), DAPI (blue) and vimentin (magenta) reveals alignment of hiPSC-CMs. (FIG. 12B) Cardiomyocytes on LQT2 EHS stained with α-actinin (green) and F-actin (red) had striations typical of sarcomeric structures (inset scale bar=10 μm). (FIG. 12C) Confocal images of the EHS in (FIG. 12A) display the distribution of cardiomyocytes (stained for cardiac troponin I, green) and non-myocytes (stained for vimentin, magenta). Images were taken at intervals of 1.7 μm from the surface of the EHS. Cell nuclei are indicated by DAPI staining in blue. (FIG. 12D) An orthogonal slice of the entire volume reveals multiple layers of cells, with cardiomyocytes on the surface (top arrow) and non-myocytes underneath, closest to the ECM of the slice (bottom arrow). (FIG. 12E) Activation map of EHS with LQT2 hiPSCCMs paced at 1000 ms cycle length shows anisotropic conduction. Black lines are isochrones at 40 ms intervals. Rectangular symbol indicates pacing site. (FIG. 12F) Average traces for wild type (WT, black) and LQT2 (blue) EHS paced at 1000 ms cycle length reveal differences in action potential morphology. (FIG. 12G) APD80 and APD30 were greater in LQT2 EHS versus WT EHS at 1000 ms and 700 ms paced cycle lengths. Error bars denote standard deviation. n=5 for WT EHS and n=3 for LQT2 EHS;

FIG. 13A, FIG. 13B, and FIG. 13C show the action potential morphologies and qRT-PCR analysis of ion channel transcripts. Related to FIG. 4. Sample action potential traces (FIG. 13A) illustrate the differences in action potential shape of EHS and monolayers (d40-70). Action potential durations (FIG. 13B, APD80 values are connected using solid lines and APD30 values are connected by dashed lines) plotted for pacing cycle lengths ranging from 2000 ms to 500 ms. Error bars denote standard deviation. * indicates $p<0.05$ when comparing mean APD80 for monolayers and mean APD80 for EHS at the specified cycle length. & indicates $p<0.05$ when comparing mean APD30 for monolayers and mean APD30 for EHS at the specified cycle length. n=28-31 for EHS and n=15-16 for monolayers. (FIG. 13C) Expressions of ion channel transcripts were altered in d69 EHS compared to control d22 hiPSC-CMs prior to seeding on EHS. n=3 for EHS and n=4 for controls. Error bars indicate standard deviation;

FIG. 14A, FIG. 14B, FIG. 14C, FIG. 14D, FIG. 14E, FIG. 14F, and FIG. 14G demonstrate the application of cardioactive drugs to EHS after prolonged culture and is related to FIG. 4 and FIG. 5. (FIG. 14A) Sample traces of EHS paced at 700 ms indicate the changes in action potential shape in the presence of increasing doses of Bay K 8644. (FIG. 14B) Bay K 8644 prolonged APD80, and (FIG. 14C) decreased conduction velocity in a dose-dependent manner. (FIG. 14D) Bay K 8644 also decreased the maximum capture rate. (FIG. 14E) Sample traces of d201 EHS paced at 1900 ms at baseline (black trace), after the application of 1 μM cromakalim (red trace), and after the additional application of 1 μM Bay K 8644 (green trace) indicate changes in action potential shape. (FIG. 14F) Cromakalim and Bay K 8644 both decreased APD80 and (FIG. 14G) slowed conduction velocity compared to baseline values. Baseline values of APD80 and conduction velocity before the application of drug are indicated in (FIG. 14B, C, FIG. 14F, FIG. 14G). Error bars denote standard deviation. n=3 in (FIG. 14B, FIG. 14C, FIG. 14D) and n=4 in (FIG. 14F, FIG. 14G). * indicates $p<0.05$ when comparing the percent change to 0 using paired, unequal variance t-test;

FIG. 15 shows GRIDS analysis applied to contraction data collected from monolayers of hiPSC-CMs superfused with increasing concentrations of E-4031.

Figure 16:
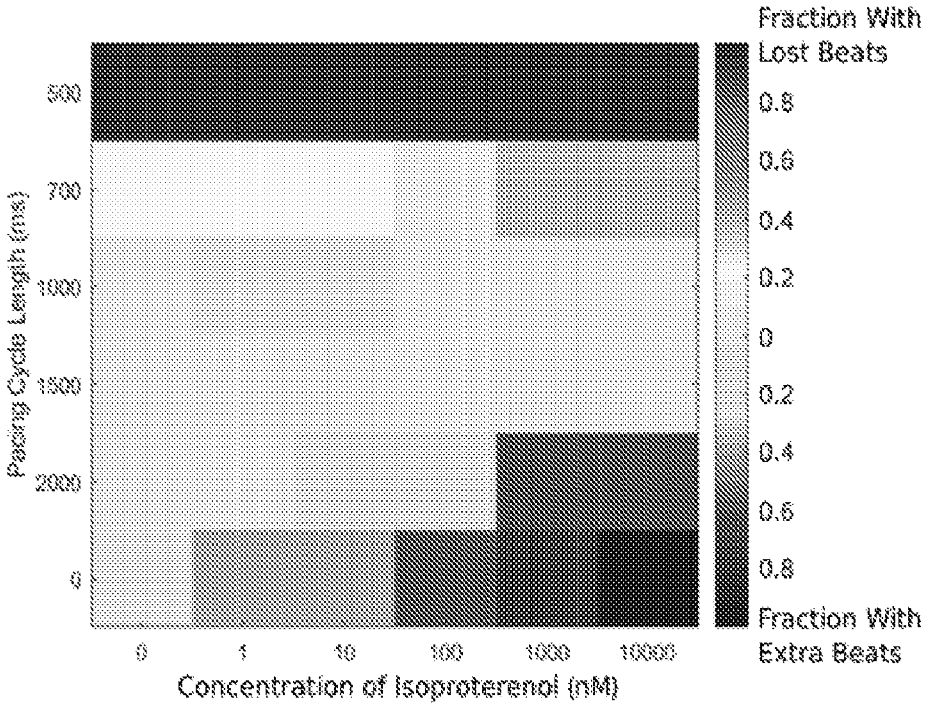

FIG. 16 shows GRIDS analysis applied to contraction data collected from monolayers of hiPSC-CMs superfused with increasing concentrations of isoproterenol.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Methods for Evaluating a Sample Comprising Cardiac Cells, Including Evaluating the Cardiac Effect of One or More Candidate Drug Compounds Drug development is a long and costly process characterized by a high degree of attrition in potential drug candidates. For example, an average of 12 years and $2.6 billion in research and development is required to bring a drug to market. Only 13.8% of drugs make it from Phase I to approval. Cardiac effect is the most common reason for withdrawing candidate drugs from the development pipeline, with 30% of drugs withdrawn during the clinical development phase (most because of adverse cardiovascular effects, Arrowsmith and Miller, 2013) and a high number of withdrawn in the post-marketing phase (Magdy et al., 2018).

As such, a need exists for accurate methods of screening drugs for cardiac effect early in the development pipeline. Disclosed herein are new analytical tools for assessing cardiac responses to candidate drugs. In particular, disclosed herein are new methods for evaluating the cardiac effect of compounds that involve measuring the response of one or more cardiac cells to a given compound at different pacing rates, thus allowing for evaluation of the rate-dependence of various ion currents that can be affected by cardiac drugs as well as the cardiac cell response over the entire dynamic range of normal and abnormal heart rates.

The advancement in cardiac differentiation strategies for human pluripotent stem cells (hPSCs) (Burridge et al., 2012) has opened up opportunities for new in vitro studies of human cardiomyocytes (CMs). Widespread and reliable use of hPSC-CMs, however, requires the development of preparations that can recapitulate essential features of myocardial structure and function: e.g., elongated CMs in arrays that mimic myofiber bundles, coordinated contraction, fast and uniform conduction of action potentials (APs), and appropriate sensitivity to cardioactive drugs. To this end, a variety of strategies have been employed to make tissue-like constructs, including casting hPSC-CMs in hydrogels (Tzatzalos et al., 2015), seeding them onto synthetic matrices (Ma et al., 2014), and fabricating cell sheets (Matsuura et al., 2012). These efforts have resulted in structurally organized, multicellular preparations that promote more mature states of cardiac gene expression, contraction, calcium handling, and conduction. Their ultimate utility for in vitro studies, however, may be hampered by the inability to maintain functionality during long-term culture and the absence of instructive cues typically present in the adult myocardium.

An emerging strategy is to use decellularized myocardial matrix as a source of biochemical, topographical, and biomechanical cues present in the heart to direct differentiation and maturation of PSC-CMs. Decellularized myocardial matrix decreases stem cell pluripotency and induces differentiation in iPSCs (Carvalho, 2012) and early cardiac progenitor cells (Lu et al., 2013). The idea that multi-component extracellular matrix (ECM) can enhance cardiac differentiation has been demonstrated with hydrogels composed of solubilized acellular porcine matrix (Duan et al., 2011) or solubilized basement membrane Matrigel preparations (Zhang et al., 2012). Cell culture coatings made from these solubilized, acellular matrix sources or from decellularized sheets of supporting cells enhance the structural organization of CMs (Baharvand et al., 2005) and temporally advance the expression of cardiac genes and proteins in cardiac progenitor cells (French et al., 2012). Acellular matrix can improve the response of single hiPSC-CMs to cardiac drugs so that they more closely resemble that of adult CMs (Feaster et al., 2015). While these findings indicate that decellularized matrix may be suited to guide cellular organization, promote CM lineage commitment, accelerate maturation, and promote better physiological responses to cardiac drugs, reseeding decellularized myocardium with hPSCs and differentiating these cells into a dense tissue-like network of CMs has proven difficult. Furthermore, an important step toward the creation of a truly tissue-like preparation of human CMs would be the demonstration of a high degree of electrophysiological and contractile function in preparations generated on decellularized matrices.

While decellularized myocardium provides biological cues that direct cardiomyocytes organization and function, repopulating it to create a highly functional electrical and mechanical syncytium has proven challenging. The presently disclosed subject matter provides, in part, engineered heart slices from thin decellularized sheets and heart cells derived from reprogrammed human skin cells, blood cells and other somatic cells that can be used for long-term electrophysiological and contractile studies and drug testing. In the presently disclosed subject matter, decellularized myocardial slices were repopulated with hiPSC-CMs to make EHS. The EHS manufactured in this way exhibited coordinated contractions and anisotropic electrical conduction; could be cultured and retained electrical and contractile function for >200 days; and had different sensitivities to ion-channel drugs than cell monolayers. As provided herein, this EHS can be used to evaluate cardiac effect of a candidate drug compound.

More particularly, described herein are methods for evaluating a sample comprising cardiac cells. The methods described herein may assess the ability of a sample comprising cardiac cells to recapitulate essential features of myocardial structure and function. For example, the methods described herein may be used to measure any number of responses that are indicative of electrophysiological maturity, physiological state and/or long-term health of a sample comprising cardiac cells. The methods involve providing at least one sample comprising one or more cardiac cells, pacing the one or more cardiac cells at two or more fixed rates; and measuring a fixed response of the one or more cardiac cells at each of the two or more fixed rates. In some embodiments, the method comprises measuring a spontaneous response of the one or more cardiac cells before pacing the cells at the two or more fixed rates.

Also described herein are methods for evaluating the cardiac effect of a compound. The method for evaluating the cardiac effect of a compound comprises obtaining at least one sample comprising one or more cardiac cells, administering the compound to each sample, pacing the one or more cardiac cells at two or more fixed rates, and measuring a fixed response of the one or more cardiac cells to the compound at each of the two or more fixed rates. The cardiac cell may be paced at the first of the two or more fixed rates before or after administration of the compound. In some embodiments, the method further comprises measuring a spontaneous response of the one or more cardiac cells to the compound prior to pacing the one or more cardiac cells at the two or more fixed rates.

For any of the methods described herein a plurality of samples may be provided, each sample comprising one or more cardiac cells. Alternatively, a single sample may be provided.

Any suitable method may be used to pace the cardiac cell at the two or more fixed rates. Pacing can be applied in multiple ways as known in the art, including through electrical and optogenetic systems.

The cardiac cell may be paced at any suitable rate. In general, the pacing rates may span the physiological and pathophysiological range appropriate for the intended species. Accordingly, the pace rates used may vary based upon the species from which the cardiac cell is derived. For example, the heart rate of smaller mammals, such as a mouse, tends to be faster than the heart rate of larger mammals, such as a human. Accordingly, selection of the appropriate pace rates will be dependent on the species of cardiac cell used. In some embodiments, the cardiac cell may be paced at two or more fixed rates, wherein each rate ranges from about 0.3 Hz (18 bpm) to about 10 Hz (600 bpm). For example, the cardiac cell may be paced at about 0.1 Hz to about 10 Hz, about 0.5 Hz to about 7.5 Hz, about 1 Hz to about 5 Hz, about 2 Hz to about 4 Hz, or about 3 Hz. For example, the cardiac cell may be paced at two or more of about 0.5 Hz, about 1 Hz, about 1.5 Hz, or about 2 Hz.

In particular embodiments, the cardiac cell may be paced about 30 beats per minute (bpm) to about 600 bpm. For example, the cardiac cell may be paced at about 30-600 bpm, about 40-500 bpm, about 50-400 bpm, about 60-300 bpm, about 70-200 bpm, about 80-190 bpm, about 90-180 bpm, about 100-170 bpm, about 110-160 bpm, about 120-150 bpm, or about 130-140 bpm. For example, the cardiac cell may be paced at about 30 bpm, about 40 bpm, about 50 bpm, about 60 bpm, about 70 bpm, about 80 bpm, about 90 bpm, about 100 bpm, about 110 bpm, about 120 bpm, about 130 bpm, about 140 bpm, about 150 bpm, about 160 bpm, about 170 bpm, about 180 bpm, about 190 bpm, about 200 bpm, about 210 bpm, about 220 bpm, about 230 bpm, about 240 bpm, or about 250 bpm. In some embodiments, each fixed rate is unique (i.e., each rate is different from each other rate). For example, in some embodiments the first fixed rate is different from the second fixed rate. In some embodiments, the cardiac cell may be paced at two or more sequentially increasing rates. In other embodiments, the cardiac cell may be paced at two or more sequentially decreasing rates.

The cardiac cell may be paced at any suitable number of fixed rates. In general, the number of fixed rates may be selected according to the needs of the user and may be dependent on the sample type used. In some embodiments, the cardiac cell may be paced at 2-20 fixed rates. For example, the cardiac cell may be paced at two fixed rates, three fixed rates, four fixed rates, five fixed rates, six fixed rates, seven fixed rates, eight fixed rates, nine fixed rates, ten fixed rates, 11 fixed rates, 12 fixed rates, 13 fixed rates, 14 fixed rates, 15 fixed rates, 16 fixed rates, 17 fixed rates, 18 fixed rates, 19 fixed rates, 20 fixed rates, or more than 20 fixed rates.

The disclosed methods involve measuring the response of the cardiac cell. In some embodiments, the disclosed methods involve measuring the response of the cardiac cell to the compound. As used herein, the term "response" indicates "spontaneous response" and/or "fixed response" unless otherwise specified. The term "spontaneous response" may refer to the response of the cardiac cell while the cell is not being paced at a fixed rate. For example, the term "spontaneous response" may refer to the response of the cardiac cell prior to pacing the cell at the first fixed rate. For example, the term "spontaneous response" may refer to the response of the cardiac cell after administration of the compound but prior to pacing the cell at the first fixed rate. The term "spontaneous response" may also refer to the response of the cardiac cell after administration of the compound after pacing has been turned off. The term "fixed response" refers to the response of the cardiac cell while the cell is being paced at a given fixed rate. For example, the term "fixed response" may refer to the response of the cardiac cell after administration of the compound and while pacing the cell at each fixed rate. In this effect, multiple fixed responses may be measured, wherein each response may be measured at each fixed rate. For example, a first fixed response may be measured while pacing at the first fixed rate, a second fixed response may be measured while pacing at the second fixed rate, a third fixed response may be measured while pacing at the third fixed rate, and so forth.

Measuring the response of the cardiac cell comprises measuring any suitable indication of cardiac excitability, automaticity, refractoriness, contraction, and/or conduction. For example, measuring the response of the cardiac cell may comprise obtaining any suitable electrophysiological recording of the cardiac cell. Suitable electrophysiological recordings include measurements of transmembrane voltage, intracellular calcium, action potential parameters, calcium transient parameters, and the like. For example, electrophysiological recordings may comprise recording of action potentials. Measuring the response of the cardiac cell may be performed using any suitable method known in the art, including multielectrode recordings, automated patch clamp, impedance measurements, voltage mapping, calcium mapping, time-lapse imaging, and the like. In some embodiments, contraction traces may be recorded. Contraction recordings may be measured using imaging, force transducers, optical indicators, and the like.

In some embodiments, measuring the response comprises measuring one or more of pace-capture, repolarization time, contraction strength, and conduction velocity. For example, pace-capture measurements may be obtained to indicate whether the cardiac cell lost beats, maintained the same number of beats, or generated extra beats compared to the number of beats at the fixed pace rate. For example, action potentials or contraction traces may be recorded to measure pace-capture of the cardiac cell. Alternatively or in combination, action potentials could be recorded to measure action potential repolarization time and/or action potential conduction velocity. Alternatively or in combination, contraction strength may be measured. Any suitable measurement or combination of measurements may be used to evaluate the sample.

Figure 6A:
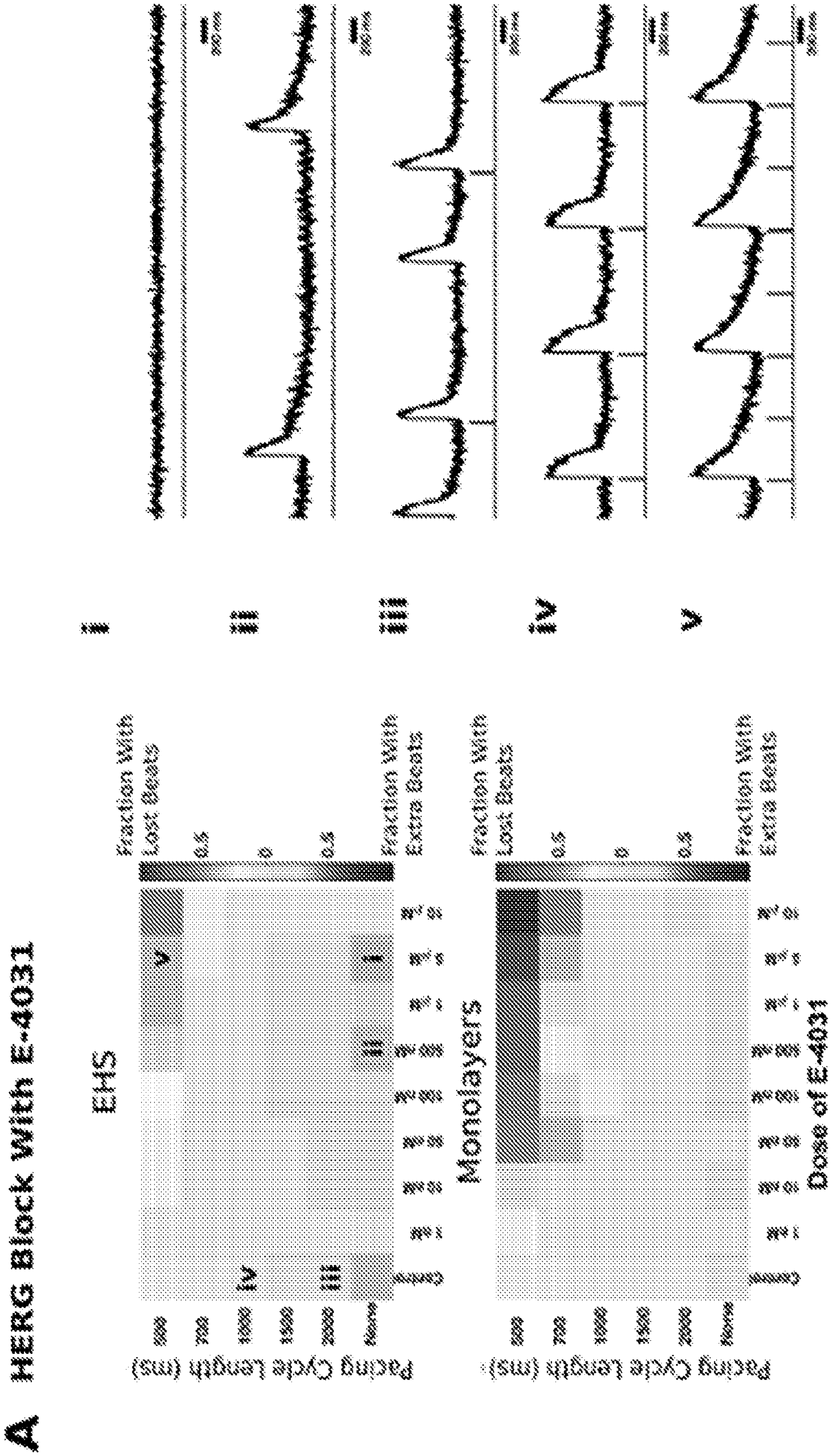

Any of the methods described herein may further comprise reporting the measured response of the one or more cardiac cells on an arbitrary classification scale. In some embodiments, the methods may further comprise reporting the measured response on a binary classification scale. For example, fractions of lost and extra beats are designated in the example in FIG. 6. For example, recordings of action potentials or contraction traces can be categorized as maintaining 1:1 pace-capture (FIG. 6A,iv), generating extra beats when paced (FIG. 6A,iii), or losing beats during capture (FIG. 6A,v). In some embodiments, the response may be reported on a binary classification scale wherein each response is categorized as above or below a certain threshold. For example, the response may be reported as whether each cardiac cell has a conduction velocity above or below a certain value. In other embodiments, the measured response may be reported on a classification scale comprising multiple thresholds. For example, the response may be reported on a tertiary classification scale, a quaternary classification scale, and the like.

Any of the methods described herein may further comprise compiling the reported spontaneous response and/or fixed response of each cardiac cell into a single visual representation. This visual representation is also interchangeably referred to herein as "GRIDS," "GRIDS map," or "grid of responses indicating drug sensitivity." For example, the spontaneous response and the fixed response at each of the two or more fixed pace rates for each cardiac cell may be compiled into a single visual representation. In some embodiments, the visual representation is color coded. For example, responses below the given threshold can be coded blue and responses above the given threshold can be coded as red. In some embodiments, responses above and below the given threshold can be color coded on a continuous color gradient. These colors are only intended to be nonlimiting examples, other colors could be substituted according to individual preference.

In some embodiments, the methods further comprise assessing the cardiac effect of the compound based upon the measured response of the one or more cardiac cells to the compound. The term "cardiac effect" as used herein refers to the impact of the compound on cardiac function. For example, cardiac effect may indicate an alteration in cardiac function or no change in cardiac function. Alterations in cardiac function may be impaired cardiac function or enhanced cardiac function. In some instances, impaired cardiac function may indicate cardiotoxicity of a drug. For example, in some instances it would be undesirable to have a drug that causes cardiac dysfunction or damage, which may be manifested as extra beats leading to elevated arrhythmia risk or lost beats leading to conduction block. In other instances, it may be desirable to identify a drug that causes changes in cardiac function. For example, it may be desirable to identify a drug that causes lost beats for use in pathophysiological conditions that cause abnormally high pacing rates. As another example, it may be desirable to identify a drug that produces extra beats for use in pathophysiological conditions that cause very low pacing rates or as a candidate for patients with elevated arrhythmia risk.

In some embodiments, cardiac effect may be indicated by one or more electrophysiological differences following addition of the compound. For example, cardiac effect of the compound may be indicated by differences in one or more of cardiac excitability, automaticity, refractoriness, and/or conduction following addition of the compound. For example, cardiac effect of the compound may be indicated by abnormal pace-capture measurements (i.e. lost beats or extra beats), changes in repolarization time, changes in contraction strength, and/or changes in conduction velocity.

In particular, the disclosed methods allow for evaluation of compounds at fixed pacing rates, thus more effectively mimicking daily or day-to-day physiological conditions in which the heart rate is not constant. For example, heart rate may vary from one day to the next, during sleep, wakefulness, the stress response, exercise conditions, and the like. Accordingly, the disclosed methods enable a more realistic evaluation of the cardiac effect of compounds compared to methods currently used in the art.

In some embodiments, the disclosed methods may be used for testing of a single compound. In other embodiments, the disclosed methods may be used for testing multiple compounds. For example, the method may be used to test the effects of multiple compounds, wherein the multiple compounds are added to the sample simultaneously. Alternatively, multiple compounds may be added to the sample sequentially. Such embodiments may be useful in conditions where compounds are intended for simultaneous or sequential use in a subject. In some embodiments, the disclosed methods may be adapted for use in high-throughput drug screens.

The methods described herein may be used on any suitable sample. Any type of cardiac cell may be used in the disclosed methods. Suitable cardiac cells include human induced pluripotent stem cell-derived cardiomyocytes (hiPSC-CMs), embryonic stem cell-derived cardiac cells, directly reprogrammed cells (from fibroblasts or other somatic cells), natural cardiac cells isolated from native tissue (both human and animal), and various cardiac cell lines. In some embodiments, a computer model of a cardiac cell may be used. The sample may be a single cell, a cell monolayer, a cell cluster, engineered cardiac tissue, cardiac organoid, cardiac tissue explant, or whole heart. In particular embodiments, the sample may comprise engineered heart slices (EHS), as described in U.S. Pat. No. 10,183,097 for Engineered Cardiac Derived Compositions and Methods of Use, to Tung and Blazeski, issued Jan. 22, 2019, the entire contents of which are incorporated herein by reference.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Functional Properties of Engineered Heart Slices Incorporating Human Induced Pluripotent Stem Cell-Derived Cardiomyocytes Human induced pluripotent stem cell-derived cardiomyocytes (hiPSC-CMs) hold great promise for cardiac studies, but their structural and functional immaturity precludes their use as faithful models of adult myocardium. The presently disclosed subject matter provides engineered heart slices (EHS), preparations of decellularized porcine myocardium repopulated with hiPSC-CMs that exhibit structural and functional improvements over standard culture. EHS exhibited multicellular, aligned bundles of elongated CMs with organized sarcomeres, positive inotropic responses to isoproterenol, anisotropic conduction of action potentials, and electrophysiological functionality for more than 200 days.

In some embodiments, the presently disclosed subject matter provides a drug assay, referred to herein as "GRIDS," that serves as a "fingerprint" of cardiac drug sensitivity for a range of pacing rates and drug concentrations. GRIDS maps characterize differences in drug sensitivity between EHS and monolayers more clearly than changes in action potential durations or conduction velocities. EHS represent a tissue-like model for long term culture, structural and functional improvement, and higher fidelity drug response of hiPSC-CMs.

Methods

Preparation of Engineered Heart Slices (EHS)

Slices of porcine myocardium 12 mm in diameter and 300 μm in thickness were sectioned and decellularized as previously described (Blazeski et al., 2015). The dECM slices were spread on plastic 12-mm diameter coverslips, with the perimeter of each slice wrapped around the edges of the coverslip. Coverslips with slices were placed in wells of standard 24-well culture plates and kept in PBS with antibiotics for up to 2 weeks prior to reseeding.

hiPSC Differentiation and Culture

Wild type (WT) and LQT2 hiPSC lines with a heterozygous A422T mutation in the hERG channel (Spencer et al., 2014) were gifts from Dr. Bruce Conklin. Both hiPSC lines were differentiated using a monolayer-based protocol (Boheler et al., 2014; Wang et al., 2015). The age of the EHS (d26 to d201) is given as the time in days from the start of hiPSC-CM differentiation (d0). On d9, the medium was switched to RPMI 1640 containing B-27 with insulin, and this medium was used for the remainder of time both prior to and after seeding on the dECM slices.

On d10-12, hiPSC-CM monolayers were dissociated using 0.05% Trypsin-EDTA and plated on dECM slices affixed to coverslips at a density of 0.8 to 1.3 million cells/cm$^2$. EHS were maintained in culture for 16 to 191 days prior to evaluation by optical mapping or contraction measurements.

Imaging of Extracellular Matrix and EHS

Standard fixation and immunostaining techniques were applied to slices before and after decellularization to label F-actin, nuclei, collagen I, collagen III, and laminin. Unstained dECM slices were also imaged by second harmonic generation (SHG). EHS were fixed and stained using standard techniques for cardiac troponin I (cTnI), α-actinin, connexin 43 (Cx43), vimentin, F-actin, and nuclei (DAPI). All samples were imaged by confocal microscopy. Nuclear elongation and orientation were analyzed in confocal images of EHS and monolayers using custom MATLAB scripts. Cellular structures in EHS were imaged by transmission electron microscopy.

Contraction Measurements

WT d24-78 EHS were placed in a 35-mm tissue culture mm dish filled with Tyrode's solution and maintained at 31±0.1° C. for the duration of the experiment. A section of each EHS was detached from the edge of the coverslip so that it could move freely. Each EHS was paced at 1 Hz, 1.5 Hz, and 2 Hz while the free region was imaged with a CCD camera. A custom MATLAB script was used to segment the image and calculate the change in EHS area over time, which was used as a measure of contraction.

Electrophysiological Studies

Each EHS was placed in Tyrode's solution and stained with 10 μM di-4-ANEPPS for 10 min at 37° C. The EHS was rinsed several times in a dish with warm Tyrode's solution, and then immersed in Tyrode's solution containing 10 μM blebbistatin to suppress contraction. The dish was placed on a 37° C. heated stage for the duration of the experiment. At least 5 min after adding blebbistatin, the EHS was stimulated with a point electrode and optically mapped using a CMOS camera (MiCAM Ultima-L, SciMedia). The EHS was paced by 5 ms monophasic rectangular pulses at stepwise increasing rates starting at 0.5 Hz. For some samples, E-4031, chromanol 293B, nifedipine, Bay K 8644, $BaCl_2$, or cromakalim was added for 7 min prior to mapping. Mapping data were analyzed using custom MATLAB scripts (details provided in Supplemental Information). AP durations at 30% and 80% repolarization (APD30 and APD80) were calculated from the optical voltage signal. For drug studies, APD and conduction velocity (CV) measurements at each concentration were plotted as a percentage of APD and CV measured at baseline, with no drug present.

Statistics

All data are presented as mean±SD. A Wilcoxon Rank-Sum test was used to determine statistical significance between control and drug groups for WT EHS contraction experiments, and between WT and LQT2 EHS. Paired, unequal variance, two-tailed t-tests were used for statistical tests of significance between experimental groups in all other drug studies, and unpaired, unequal variance, two-tailed t-tests were performed to determine the statistical significance between experimental measurements of d62-82 and d201 EHS. Differences were considered statistically significant at $p<0.05$.

Representative Results

Thin Slices of Decellularized Myocardium Promote Growth and Global Alignment of hiPSCCMs.

12-mm diameter plugs of left ventricular myocardium from porcine hearts were sectioned into 300-μm thick slices using a vibratome (FIG. 1A). Full decellularization was achieved after 3.5 hours of exposure to detergents (FIG. 1B). The resulting thin dECM slices did not maintain their shape when removed from liquid, a problem that was resolved by spreading each slice onto a plastic coverslip. Under these conditions, the perimeter of the dECM slice could adhere to the edges of the coverslip (FIG. 1C). The dECM slice exhibited overall alignment of ECM and residual vasculature (FIG. 1D). The removal of cells and nuclei was confirmed by assaying slices before and after treatment with detergents. Native slices contained an abundance of cells, indicated by nuclear staining and intracellular F-actin (FIG. 8A), which were absent in dECM slices (FIG. 8E).

Decellularization left intact the ECM components of collagen I (FIG. 8B, FIG. 8F), collagen III (FIG. 8C, FIG. 8G), and laminin (FIG. 8D, FIG. 8H). The organization of collagen fibers in the dECM slice, as visualized by SHG imaging, was not altered by storing sectioned slices at −80° C. prior to decellularization or by storing ventricular plugs at −80° C. prior to slicing and decellularization (FIG. 8, FIG. 8I, FIG. 10J, FIG. 8K, FIG. 8L). Overall, each component analyzed in the dECM slices largely retained the structural alignment observed in native slices. The presently disclosed decellularization method decreased the DNA content of slices more than 160-fold to approximately 0.12 μg/mg initial dry weight, as previously reported (Blazeski et al., 2015). Taken together, these data indicate that the detergent-treated slices are almost completely devoid of cells and nuclei but retain a mixture of ECM components that remains structurally organized.

Figure 9:
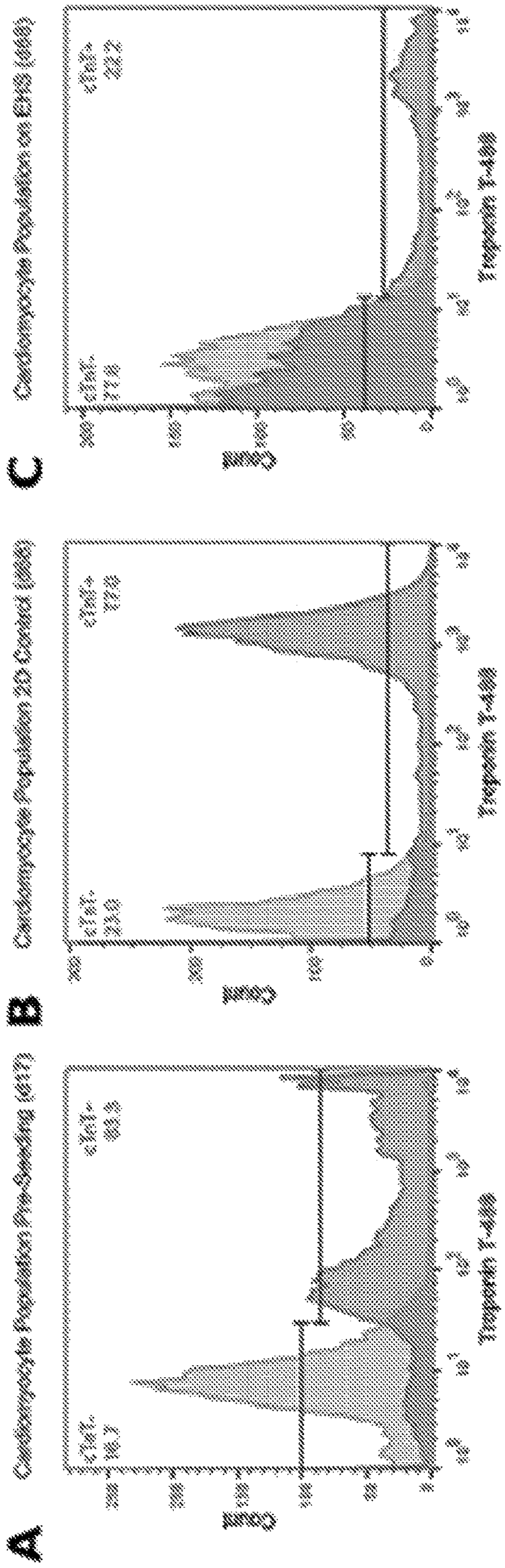
Figure 10:
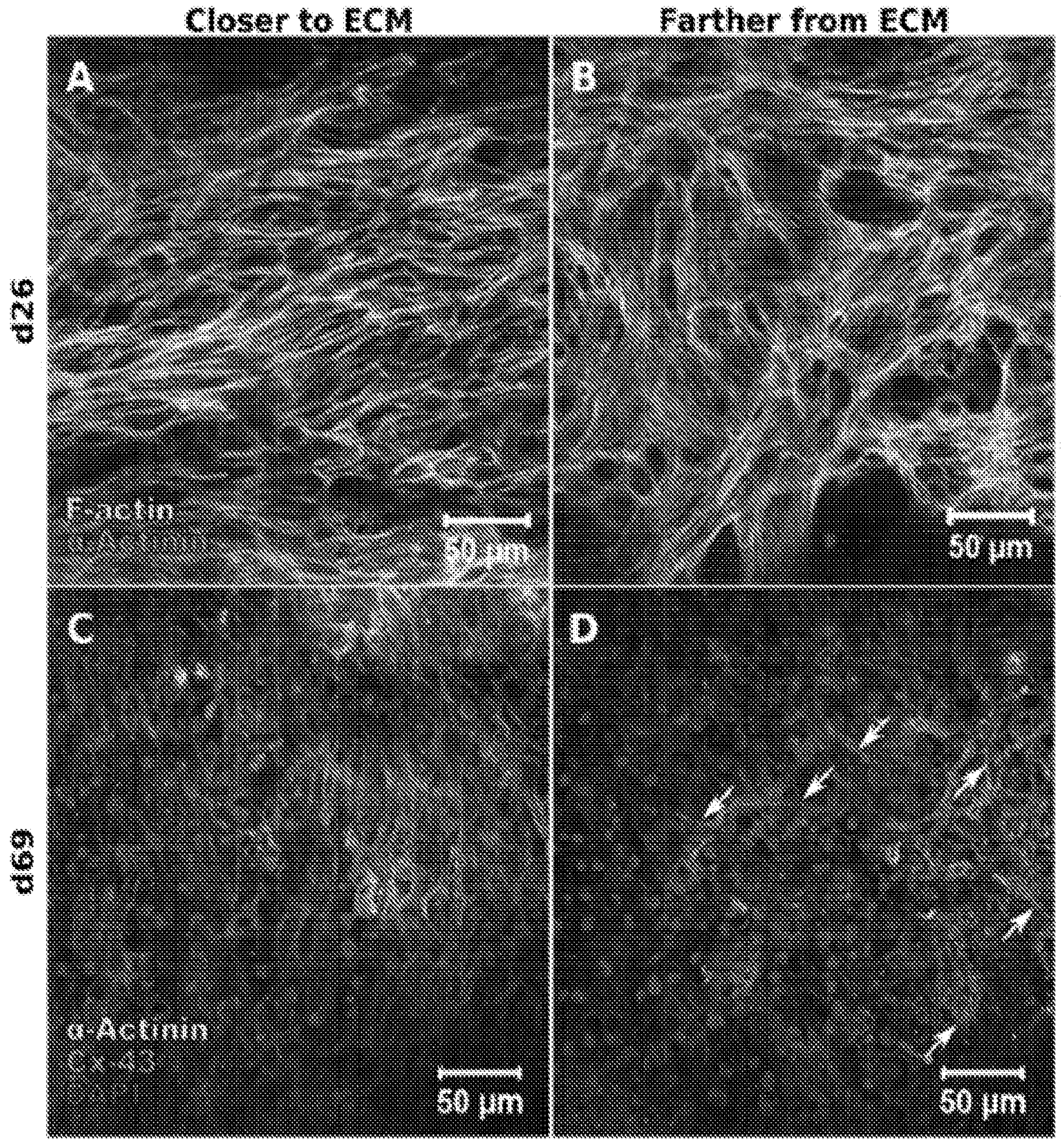

Differentiated progeny from hiPSCs were seeded onto the dECM slices at d10-12 (FIG. 1A) to form EHS. The presently disclosed cardiac differentiation protocol yielded a mixture of, on average, approximately 83% cTnT-positive hiPSC-CMs and approximately 17% cTnT-negative non-CMs (FIG. 9A, FIG. 9B). After 16 days of EHS culture (d26-28), these cells formed multicellular, aligned tissue layers (FIG. 2A, FIG. 2B). CM alignment, however, decreased in the apical cell layers farthest away from the surface of the matrix (FIG. 10). Cells, which organized into multicellular strands, were made up mainly of cTnIpositive CMs with vimentin-positive non-CMs located primarily in the center of the strands (FIG. 2A). CMs also exhibited striations characteristic of sarcomere structures and stained positively for Cx43 (FIG. 4C) localized along the periphery of the cells (FIG. 10D). Transmission electron micrographs of hiPSC-CMs on slices showed the presence of z-lines in sarcomeres that were surrounded by mitochondria (FIG. 2D).

Comparisons were then made between d55 hiPSC-CMs seeded at low density to make EHS and those on Geltrex-coated cell culture dishes to evaluate the effect of the matrix on cellular shape and organization. CMs grown on Geltrex were cobblestone-like and had randomly-oriented sarcomeres (FIG. 2E). Age-matched CMs on EHS were elongated, with sarcomeres arranged along the long axis of each cell (FIG. 2F). Interestingly, the morphological trait of elongated cells and aligned sarcomeres became ingrained with time on the tissue slices.

For example, when hiPSC-CMs were maintained for a prolonged period of time (139 days) as EHS and subsequently dissociated and replated under standard 2D culture systems, the cultivated cells retained an elongated morphology and exhibited highly organized sarcomeres (FIG. 2G). Cellular alignment on the dECM slice was assessed by the orientation and elongation ratio (long axis/short axis) of nuclei fitted by ellipses (FIG. 2H, FIG. 2I). In hiPSC-CMs cultured on Geltrex in standard cell culture dishes, the nuclear elongation ratio was 1.38±1.21 with an SD of 56.6 degrees around the mean angle of orientation (n=165 nuclei, FIG. 2J). The nuclei of CMs cultured as EHS were more elongated and more closely oriented in the same direction, having an elongation ratio of 1.70±1.37 and an SD of 50.1 degrees around the mean angle of orientation (n=233 nuclei, FIG. 2J).

EHS Contract Synchronously and Respond to Isoproterenol.

Spontaneous and asynchronous contractions were apparent in EHS within 24 hours of cell seeding, but this transitioned to synchronous contractions in about one week's time. At d28 and d74, we evaluated contraction as the change in EHS area in a region where the slice edge was freed from the coverslip. The contracting hiPSC-CMs deformed the ECM, permitting the change in area to be monitored as an approximation of the degree of contraction. When stimulated at a pacing cycle length (PCL) of 666 ms (1.5 Hz, n=8), the EHS area in the field of view decreased, on average, by 2.0±1.3% from its value at rest (FIG. 3A, FIG. 3B, FIG. 3C). The addition of 1 μM isoproterenol resulted in a 1.5±0.6-fold larger area change, and subsequent washout of the drug brought the area change back down to 1.1±0.4 times the baseline value (FIG. 3D).

Increasing the pacing rate from 1.5 Hz (666 ms PCL) to 2 Hz (500 ms PCL) resulted in an area change of 0.7±0.1 (negative force-frequency relationship) that was statistically significant, whereas decreasing the pacing rate from 1.5 Hz to 1 Hz (1000 ms PCL) resulted in an area change (1.1±0.1) that was not statistically significant (FIG. 11B).

EHS Exhibit Anisotropic Electrical Conduction and Retain Functionality During Long-Term Culture.

EHS at d54-58 could be pace-captured starting from a PCL of 1000 ms down to 425±51 ms (n=6) and exhibited propagation of APs throughout the entire preparation (FIG. 4A). APDs showed physiological rate-dependence: APD30 and APD80 decreased during incremental increases in pacing rate (incremental decreases in PCL from 1000 ms down to 400 ms, n=4-6) (FIG. 4C, Table 1). Both transverse and longitudinal CV showed physiological rate dependence, decreasing with increasing pacing rate (FIG. 4D). The resultant CV anisotropy ratio remained relatively constant around 1.4 over the range of PCLs from 500 ms to 1000 ms (FIG. 4E), suggesting that the increases in pacing rate primarily affected sodium channel availability (i.e., excitability) and did not cause significant changes in gap junctional conductance (de Diego et al., 2011).

TABLE 1

Electrophysiological measurements of d54-58 EHS. APD30, APD80, longitudinal and transverse conduction velocities, and anisotropy ratios correspond to plots in FIG. 2. Data represent mean ± SD.

| Paced Cycle Length (ms) | n | $APD_{30}$ (ms) | $APD_{80}$ (ms) | Longitudinal Conduction Velocity (cm/s) | Transverse Conduction Velocity (cm/s) | Anisotropy Ratio |
|---|---|---|---|---|---|---|
| 400 | 4 | 129 ± 3 | 183 ± 6 | 8.9 ± 1.5 | 7.4 ± 1.0 | 1.2 ± 0.1 |
| 500 | 6 | 152 ± 15 | 214 ± 20 | 11.6 ± 2.1 | 8.3 ± 1.7 | 1.4 ± 0.2 |
| 600 | 6 | 165 ± 19 | 235 ± 23 | 13.6 ± 2.1 | 9.7 ± 1.7 | 1.4 ± 0.1 |
| 700 | 6 | 178 ± 24 | 253 ± 29 | 15.4 ± 2.4 | 10.9 ± 1.8 | 1.4 ± 0.1 |
| 800 | 6 | 186 ± 28 | 267 ± 32 | 16.6 ± 1.8 | 11.4 ± 0.9 | 1.5 ± 0.1 |
| 900 | 6 | 198 ± 24 | 283 ± 34 | 18.9 ± 2.3 | 13.0 ± 1.3 | 1.5 ± 0.2 |
| 1000 | 6 | 211 ± 21 | 295 ± 32 | 18.8 ± 1.3 | 13.4 ± 1.4 | 1.4 ± 0.1 |

The high degree of electrophysiological function in EHS was applicable to other hiPSC lines. This was demonstrated through the analyses of EHS made with hiPSC-CMs derived from a patient with confirmed LQT2. LQT2 is a cardiac disorder characterized by prolonged ventricular repolarization arising from mutations in the rapid delayed potassium channel (hERG) that increases the incidence of arrhythmias (Tester and Ackerman, 2014). As with WT EHS, LQT2 EHS cells were aligned and organized into multicellular strands (FIG. 12A, FIG. 12B), in which non-CMs were in contact with the ECM while the CMs were organized on top of these cells (FIG. 12C, FIG. 12D). Like previous observations in WT EHS, LQT2 EHS exhibited anisotropic propagation of APs throughout the slice (FIG. 12E). APDs in LQT2 EHS were prolonged compared with those in WT EHS (FIG. 12F), recapitulating the hallmark of LQT (FIG. 12G, n=3 LQT2 EHS and n=5 WT EHS).

In addition to having structurally elongated and organized CMs (FIG. 2G), EHS in long-term culture retained cell-connectivity and paceable, coordinated AP activity. Samples that were maintained in culture for more than 2 months (d62-82) exhibited isotropic propagation of APs, typical of thicker cell layers where cells become more randomly oriented (FIG. 10), and had CVs ranging from 13.9±1.9 cm/s at 700 ms PCL to 18.4±1.8 cm/s at 1900 ms PCL (FIG. 5A, Table 2). The proportion of non-CMs in EHS at d68 increased from that at the time of seeding (FIG. 9). EHS using the same batch of cells but cultured for more than 200 days, exhibited lower CVs, which at 1300 ms and 1500 ms PCL reached statistical significance when compared to d62-82 CVs at the same PCL (FIG. 5A, Table 2). Notably, d201 EHS could be paced over a wider range of CLs, from 2000 ms (now possible because of their lower spontaneous beating rates) down to 400 ms (now possible because of their shorter APDs), than that for d62-82 EHS, from 1900 ms PCL down to 700 ms. Mean APD80 and APD30 of d201 EHS were significantly shorter at all PCLs than those of d62-82, respectively (FIG. 5C, Table 2), reflecting net increase in inward and/or net decrease in outward AP current in older EHS.

TABLE 2

Electrophysiological measurements of d62-82 and d201 EHS. APD30, APD80, and conduction velocities correspond to plots in FIG. 3. Data represent mean ± SD.

| Paced Cycle Length (ms) | $APD_{30}$ (ms) d62-82 (n = 3) | $APD_{30}$ (ms) d201 (n = 5) | $APD_{80}$ (ms) d62-82 (n = 3) | $APD_{80}$ (ms) d201 (n = 5) | Conduction Velocity (cm/s) d62-82 (n = 3) | Conduction Velocity (cm/s) d201 (n = 5) |
|---|---|---|---|---|---|---|
| 400 | — | 93 ± 14 | — | 139 ± 19 | — | 9.5 ± 1.5 |
| 500 | — | 111 ± 11 | — | 162 ± 16 | — | 11.1 ± 1.5 |
| 700 | 172 ± 15 | 128 ± 16 | 250 ± 17 | 184 ± 21 | 13.9 ± 1.9 | 12.3 ± 1.7 |
| 900 | 187 ± 19 | 137 ± 15 | 271 ± 21 | 194 ± 20 | 15.9 ± 1.7 | 13.2 ± 1.8 |
| 1000 | 196 ± 22 | 143 ± 15 | 286 ± 25 | 202 ± 21 | 16.6 ± 1.8 | 13.8 ± 1.9 |
| 1300 | 209 ± 25 | 149 ± 19 | 301 ± 30 | 209 ± 23 | 17.8 ± 1.6 | 14.4 ± 2.0 |
| 1500 | 220 ± 30 | 153 ± 18 | 312 ± 31 | 213 ± 23 | 18.1 ± 1.5 | 14.6 ± 2.0 |
| 1700 | — | 155 ± 18 | — | 215 ± 22 | — | 15.1 ± 1.7 |
| 1900 | 231 ± 33 | 153 ± 18 | 323 ± 37 | 212 ± 22 | 18.4 ± 1.8 | 15.4 ± 1.3 |
| 2000 | — | 160 ± 19 | — | 220 ± 21 | — | 16.0 ± 1.3 |

EHS Differ from Standard Monolayer Cultures in their Response to Ion Channel Modulating Drugs, when Evaluated Using GRIDS Analysis.

Based on the improved adult-like cellular morphology, more ventricular-like APs (FIG. 13A, FIG. 13B) and increased expression levels of numerous ion channel transcripts of hiPSC-CMs after culture on EHS (FIG. 13C), it was hypothesized that cells on EHS would exhibit differences in drug responses when compared with standard culture. To test the responsiveness of EHS to ion channel modulators, an assay referred to herein as "GRIDS" (grid of responses indicating drug sensitivity) was developed that characterizes the ability of a cardiac preparation to respond to pacing when exposed to a range of drug concentrations. This assay was used to compare EHS to age-matched monolayer cultures. APs of EHS and monolayers were evaluated at each drug concentration in the absence of pacing and when subjected to electrical stimulation at PCLs ranging from 2000 ms to 500 ms. By incorporating a range of pacing rates, GRIDS manifests the distinct sensitivities of different ion currents (Ravens and Wettwer, 1998) and their rate dependencies, and provides a "fingerprint" of drug sensitivity. Several types of responses were observed: no spontaneous activity (FIG. 6A,i), spontaneously generated APs when no pacing was applied (FIG. 6A,ii), extra APs in between pacing stimuli (FIG. 6A, iii), one AP generated for each pacing stimulus—i.e., 1:1 pace-capture (FIG. 6A, iv), and failure to maintain 1:1 pace-capture (lost beats) (FIG. 6A,v). The effects of each drug on augmenting paced activity was evaluated by counting the proportion of EHS and monolayers that exhibited extra beats between paced beats ('Fraction With Extra Beats', exemplified in FIG. 6A,ii-iii) and on the ability to retain capture by counting the proportion of EHS and monolayers that lost beats during pacing ('Fraction With Lost Beats' exemplified in FIG. 6A,v). Further, if application of a drug resulted in spontaneous activity, the EHS or monolayer was counted as having extra beats and included in the "Fraction With Extra Beats" visualized in the bottom row of each GRIDS analysis.

EHS and monolayers were superfused with the rapidly activating potassium current (IKr) blocker, E-4031, at concentrations ranging from 1 nM to 10 μM (FIG. 6A). At increasingly shorter PCLs, a greater fraction of monolayers than EHS lost capture during rapid pacing at concentrations of E-4031 greater than 50 nM, indicating a lower sensitivity of EHS to E-4031 under these conditions. Next, the sensitivity of EHS and monolayers to IK1 block was evaluated by superfusing them with $BaCl_2$ (FIG. 6B). The spontaneous rate of both EHS and monolayers increased in a concentration-dependent manner (not shown), and this effect was greater in monolayers. At a concentration of 500 μM $BaCl_2$, monolayers were spontaneously beating at rates up to 1 Hz and could be partially pace-captured only at CLs of 1000 ms and less (light blue, yellow and red squares), while at a concentration of 1 mM nearly all monolayers were spontaneously beating faster than 2 Hz so only a small fraction could be partially pace-captured at a CL of 500 ms (FIG. 6B, bottom, medium blue square). EHS could be overdrive paced at 700 ms and 1000 ms PCL for all concentrations of $BaCl_2$ (FIG. 6B, top). At 1 mM $BaCl_2$, all of the EHS tested lost capture at 500 ms PCL. Taken together, these results indicate EHS are less sensitive to $BaCl_2$ than monolayers.

The slow delayed rectifier K+ current (IKs) was then blocked with chromanol 293B to test its effects on EHS and monolayer cultures (FIG. 6C). The fraction of monolayers exhibiting spontaneous activity when no pacing was applied was non-zero and constant at all concentrations except for 5 μM, when it was zero, and 60 μM, when all monolayers exhibited spontaneous activity (FIG. 6C, bottom). At all concentrations tested, however, both EHS and monolayers could be pace-captured at all PCLs from 2000 ms down to 500 ms (FIG. 6C).

Therefore, chromanol 293B had a limited effect on either preparation, suggesting that IKs is poorly expressed or not functionally active in both monolayers and EHS. Aside from differences in potassium channels, whether L-type calcium channels might also be differentially expressed in EHS and in monolayers was tested, so the channel blocker nifedipine was applied (FIG. 6D). As the drug concentration was increased, monolayers lost pace-capture over a wider range of PCL, whereas EHS never lost pace-capture (FIG. 6D), indicating that EHS were insensitive to nifedipine in this regard.

Figure 7A:
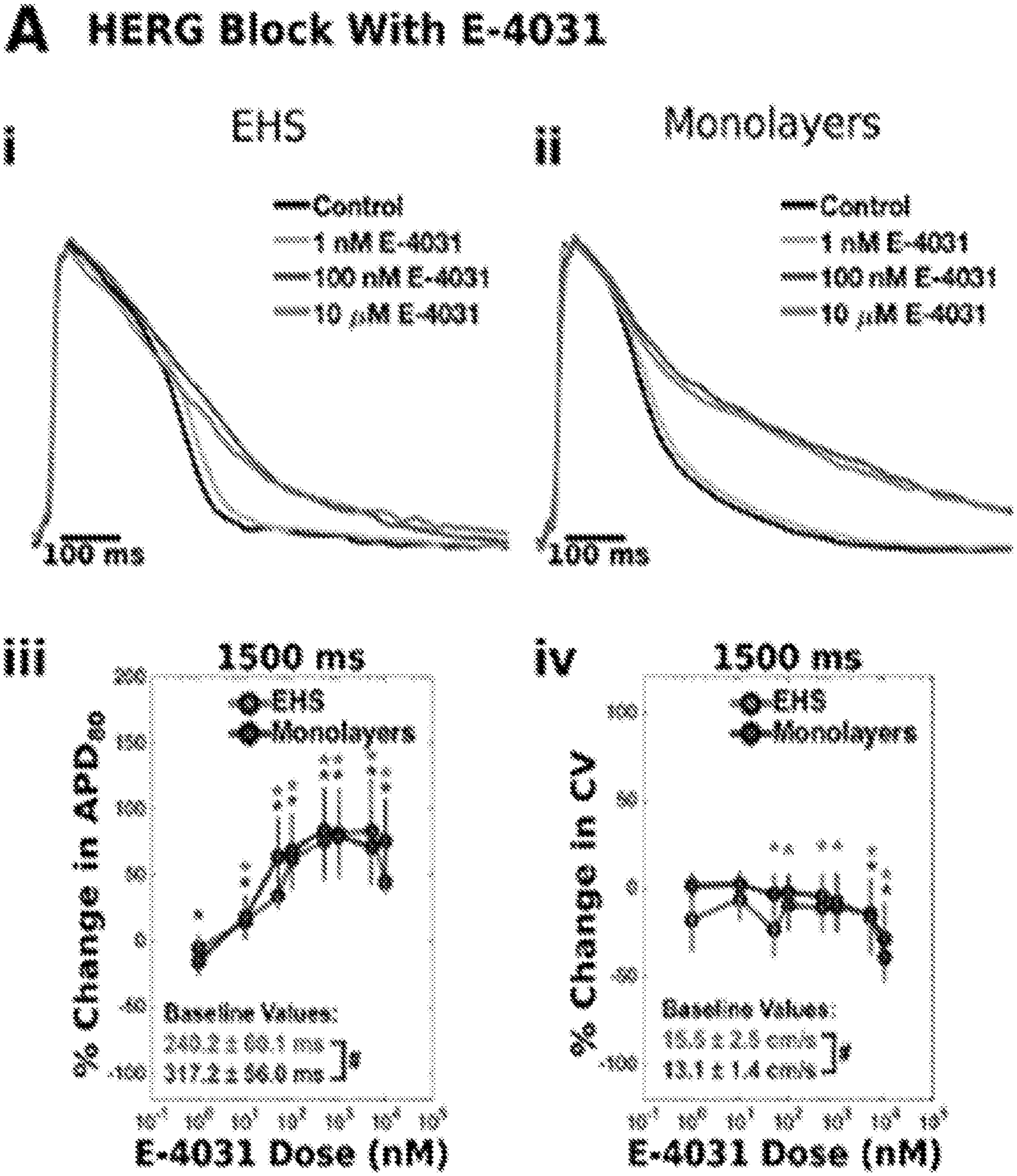
Figure 7B:
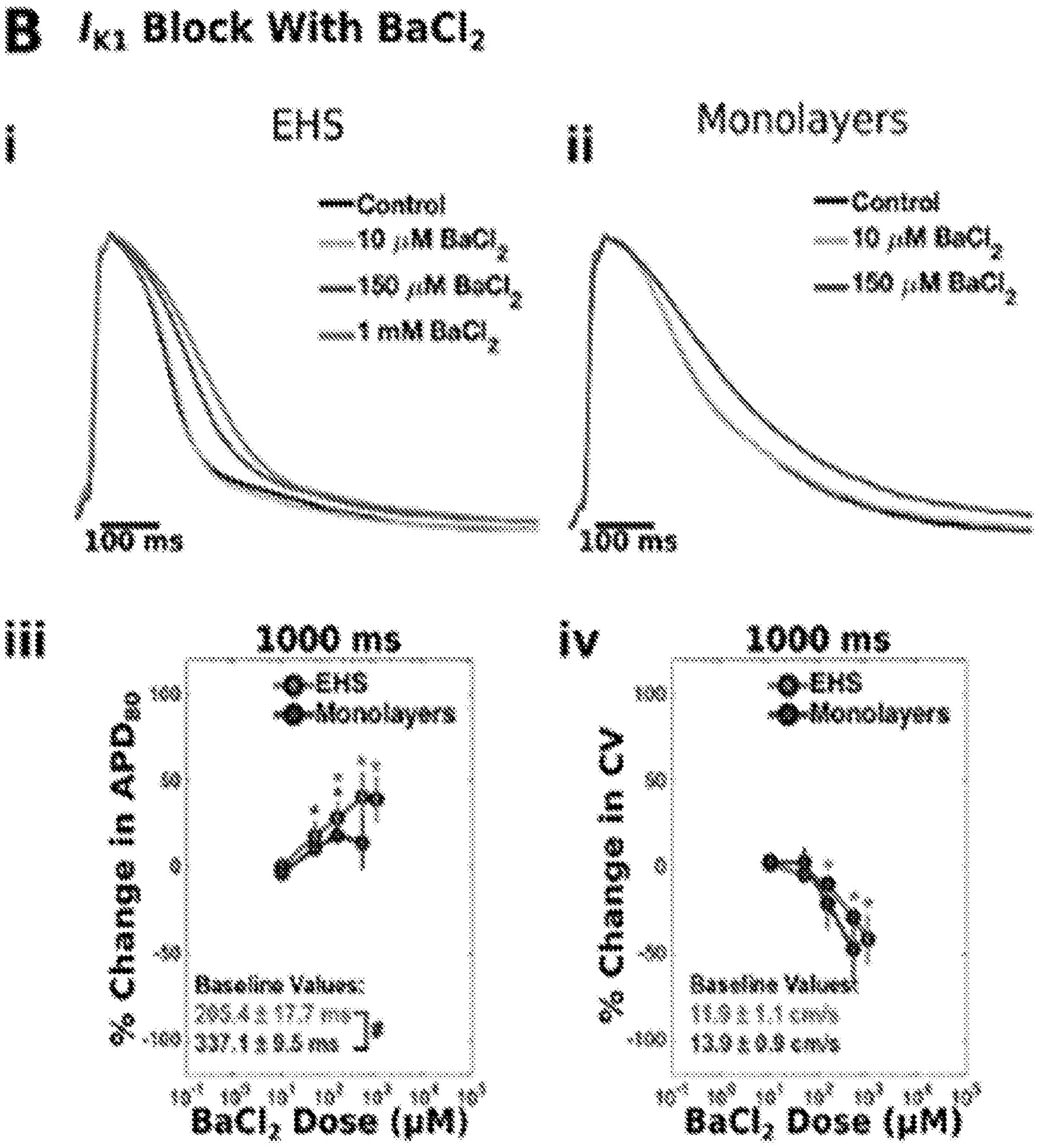
Figure 7C:
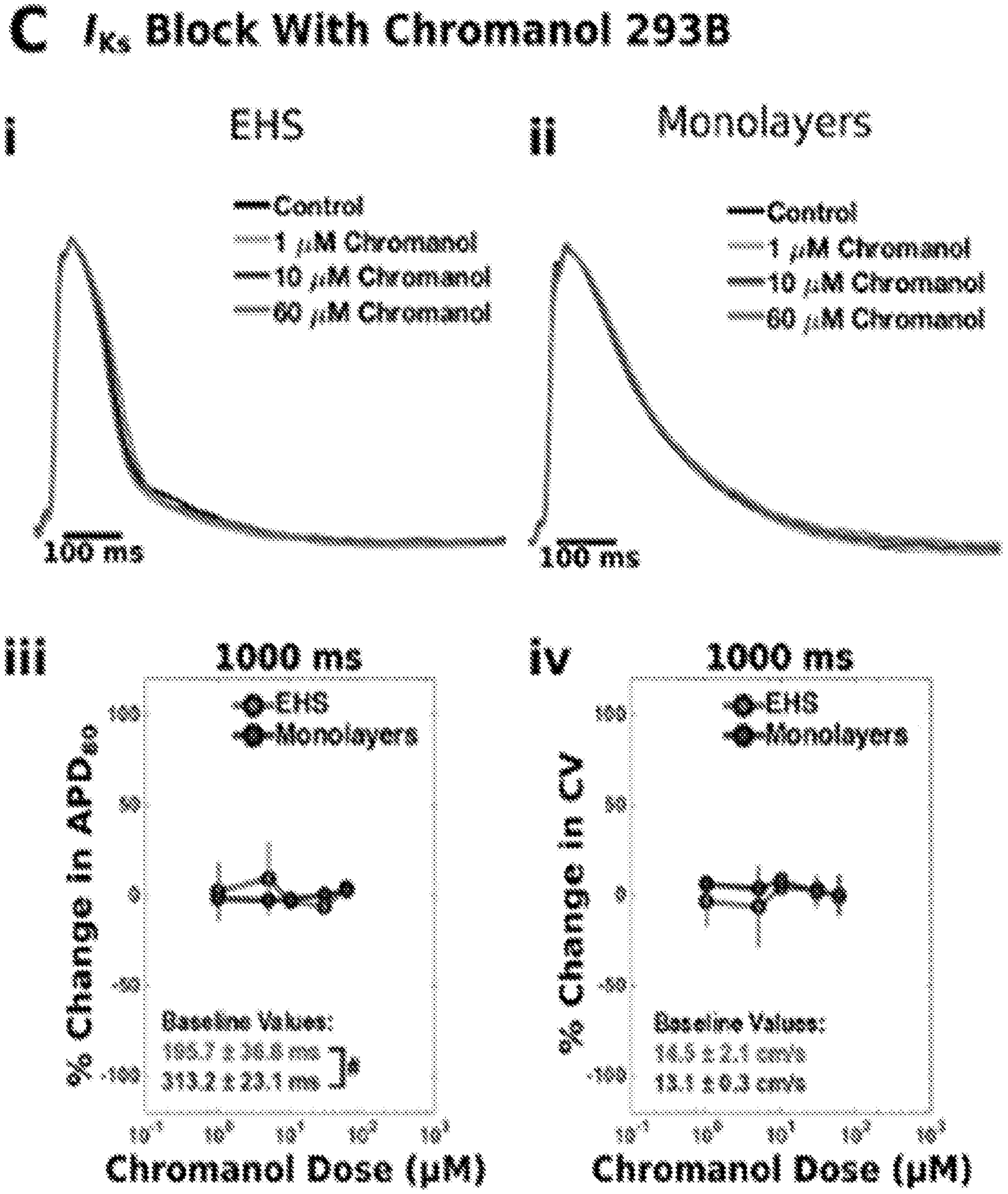
Figure 7D:
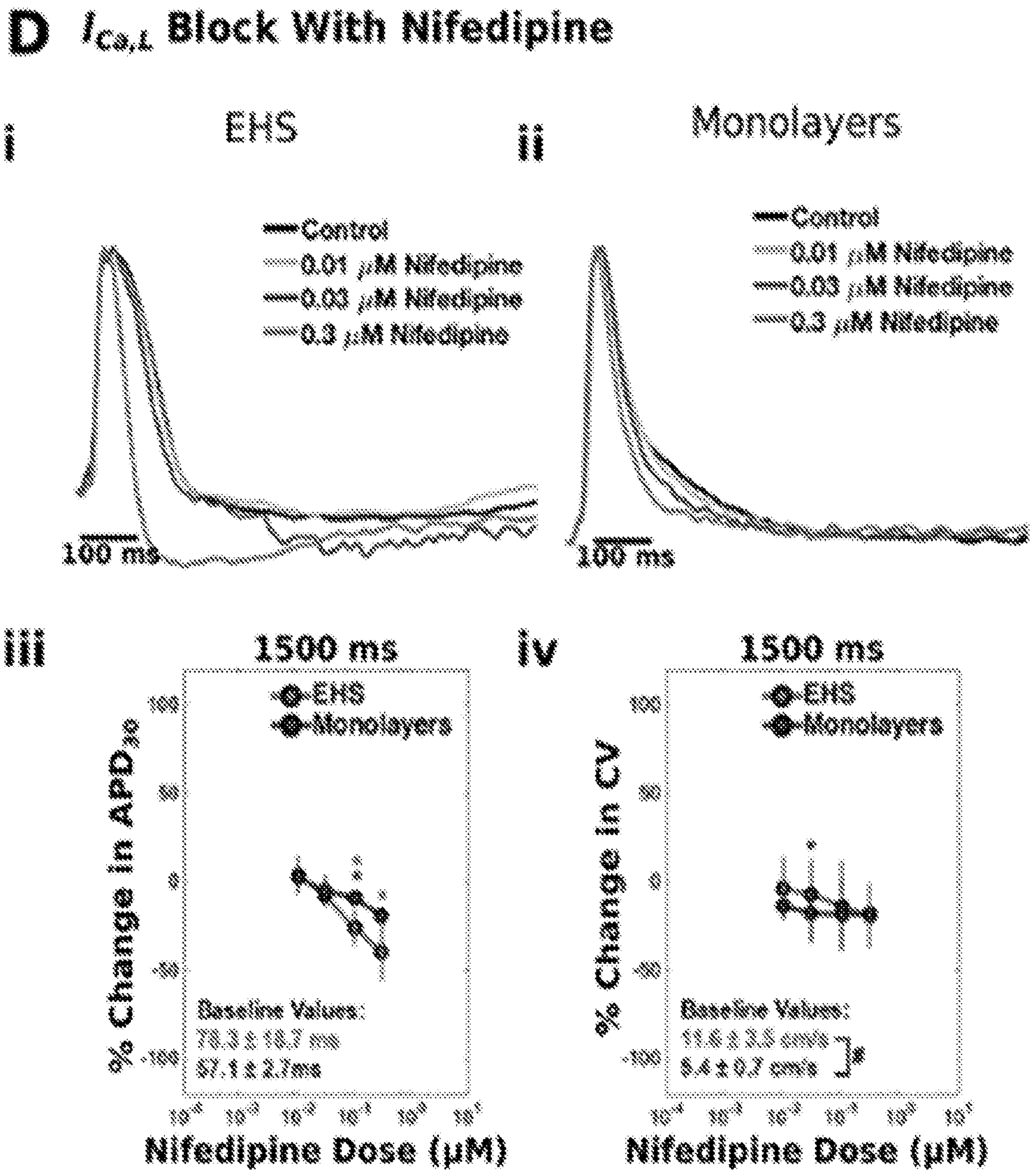

In addition to the GRIDS analysis, the occurrence of drug-induced prolongations of repolarization, which is an index of liability for acquired long-QT syndrome (Wood and Roden, 2004), as well as conduction slowing, which can be an early sign of conduction block was evaluated. At a PCL of 1500 ms, E-4031 prolonged APD80 (FIG. 7A,i-iii) and slowed CV (FIG. 7A,iv) in both EHS and monolayers in a concentration-dependent manner over a range of 50 nM to 10 μM. For concentrations up to 150 μM, $BaCl_2$ increased APD80 and decreased CV in both preparations in a concentration-dependent manner (FIG. 7B), although the decrease in CV reached statistical significance only in EHS. Chromanol 293B (FIG. 7C) had no effect on APD80 or on CV at concentrations ranging from 1 μM to 60 μM in either EHS or monolayers. Nifedipine did not affect APD80 of EHS and monolayers (not shown), but shortened the plateau phase of the AP in EHS, an effect that was quantified by APD30. At 1500 ms PCL, 0.1 μM and 0.3 μM nifedipine decreased APD30 to a greater extent in EHS than in monolayers (FIG. 7D,i-iii), suggesting that EHS have more developed ICa,L current. Nifedipine does not cause conduction slowing in healthy adult myocardium (Mitchell et al., 1982) and did not significantly decrease CV in our preparations, except at a concentration of 0.01 μM in monolayers (FIG. 7D,iv). ICa,L was further modulated in EHS by applying Bay K 8644, an L-type calcium channel activator over a range of 0.3 μM to 100 μM, and found that it increased APD and decreased CV in a concentration-dependent manner (FIG. 14A-D). Finally, it was found that EHS remained responsive to ion channel-modulating drugs even after long-term culture (d201), as in the case of Bay K 8644 and cromakalim, an activator of the ATP-dependent potassium current (IK,ATP) (FIG. 14E-FIG. 14G).

GRIDS analysis was applied to contraction data collected from monolayers of hiPSC-CMs. Each monolayer (cultured on a plastic coverslip) was placed in a 35-mm dish filled with cell culture medium and set on the stage of a microscope (LS720, Etaluma) fitted within a cell culture incubator. Monolayers were superfused with increasing concentrations of E-4031 (FIG. 15) or isoproterenol (FIG. 16), ranging from 0 to 10 μM, and paced at decreasing cycle lengths (increasing rates), ranging from 2000 ms to 500 ms, using a field electrode. At each drug dose and paced cycle length, a 30-second video of the contracting cells was recorded at a rate of 20-30 frames per second. The cellular contraction was quantified by subtracting one reference frame of video from all other frames, summing the pixels in each frame after subtraction, plotting the summed signal over time, and detecting the peaks in the signal. The peaks in each recording were analyzed to determine whether they coincided with the train of electrical stimulation pulses and the fraction of total monolayers exhibiting lost beats or extra beats at each dose and pacing rate was calculated.

When treated with E-4031 (FIG. 15, n=6), monolayers began to lose capture as the pacing rate was increased, an effect that was more pronounced at higher doses of the drug. On the other hand, isoproterenol (FIG. 16, n=6) increased the spontaneous rate of the monolayers in a dose-dependent manner, as demonstrated by the increased fraction of monolayers with extra beats when no pacing was applied (bottom row of FIG. 16) or during 2000 ms pacing. Collectively, these data demonstrate the applicability of the GRIDS method to video-based contraction analysis.

Discussion

In this study, dECM slices were repopulated with hiPSC-CMs to make EHS with coordinated and syncytial contractile and electrophysiological function. On EHS, reseeded hiPSC-CMs organize in a similar manner to the ordered arrays of fibers found in the native myocardium (Veeraraghavan et al., 2014), becoming elongated and aligned in bundles, with elongated and oriented nuclei, and well-defined, aligned sarcomeres. This is an improvement from the morphology seen in standard cultures, where hiPSC-CMs appear more cobblestone-like and have randomly-oriented sarcomeres. Gap junction staining for Cx43, however, was observed around the periphery of cells in the EHS and does not localize at intercalated discs, reflecting a level of structural immaturity that has also been found in other studies of hPSC-CMs (Zhang et al., 2013). Nevertheless, the presently disclosed EHS are a well-connected and reproducible functional syncytium of CMs that exhibits uniform conduction and coordinated contraction over an area of about 1 $cm^2$. These characteristics overcome the problem of variable and patchy conduction that occurs in other preparations using decellularized myocardium caused by non-uniform cell seeding (Guyette et al., 2016; Lu et al., 2013; Oberwallner et al., 2014).

The cellular organization of EHS and the resultant anisotropic conduction of APs is guided by the retention of the native oriented matrix in the dECM slice. This strategy to utilize the topographical cues of the ECM differs from those used in other studies to align CMs, including microcontact printing (Wang et al., 2014), hydrogel compaction in the presence of non-myocytes (Liau et al., 2011) and fabricated microgrooved (Rao et al., 2013), nanogrooved (Macadangdang et al., 2015), electrospun (Wanjare et al., 2017), and wrinkled (Wang et al., 2013) substrates. The use of decellularized matrix may confer benefits not present in the other approaches, as there is mounting evidence that the complex chemistry of the matrix can promote stem cell differentiation (Ng et al., 2011) and electrophysiological maturation of CMs (Herron et al., 2016). The presently disclosed study of EHS demonstrates the suitability of this platform to study electrophysiological function over long-term culture.

The presently disclosed experimental approach involves the routine production of batches of 10 to 20 thin tissue slices from ventricular plugs that are subsequently decellularized in parallel. This decellularization method leaves behind a scaffold that retains an organized and aligned structure, made up of multiple ECM components. While various decellularization methods have been developed (Badylak et al., 2010), the method of Ott and colleagues was selected because it preserves non-collagen proteins (particularly, fibrillin, heparin sulfate, and laminin (Guyette et al., 2016), with a trade-off of decreased retention of collagen (Akhyari et al., 2011). These noncollagen components may be particularly beneficial for promoting the differentiation and maintenance of hPSC-CMs (Nakayama et al., 2014). However, because the composition and mechanical properties of the ECM change during development of the heart from the post-natal to adult stage (Gershlak et al., 2013), further work needs to be done to identify the developmental stage that will yield ECM best suited for growth and maintenance of hPSC-CMs.

The presently disclosed method for decellularizing slices is amenable to the use of native myocardium from a variety of sources and can be used to compare the effect of different species, chamber locations, and developmental states of the ECM source on CM electrophysiology and contraction. Automation of the process of anchoring the dECM slice to a support will be necessary if large numbers of ECM scaffolds are needed to make EHS for drug discovery and screening.

While EHS exhibited a positive inotropic response to isoproterenol, their fractional shortening (around 2%) was much lower than the 30% fractional shortening reported in adult hearts (Colan et al., 1984), and they also exhibited a negative force-frequency relationship.

Further improvements, such as increasingly rapid pacing during culture, can be used to improve contractility and achieve the positive force-frequency relationship found in adult myocardium (Ronaldson-Bouchard et al., 2018). EHS also exhibited rate-dependent decreases of APD and CV, as well as anisotropic conduction, as is found in adult human heart (Yue et al., 2005).

However, CV in EHS was less than half of that measured in the adult ventricle (Durrer et al., 1970), and the anisotropy ratio of conduction was substantially less than that in the adult ventricle (Peters and Wit, 1998). The loss of CM alignment in layers of cells farther from the matrix surface likely contributed to a diminished anisotropy ratio. Amenability to long-term culture is a powerful feature of EHS, because prolonged culture advances the structural organization, cardiac gene expression, and contractile and electrophysiological function of hPSC-CMs (Lundy et al., 2013). Maintaining multi-layers of hiPSC-CMs in standard culture plates for periods of weeks is difficult, as they can detach from the underlying substrate, although individual hiPSC-CMs have been maintained for up to 120 days (Lundy et al., 2013), and multicellular embryoid bodies of hiPSC-CMs have been maintained for up to 360 days (Kamakura et al., 2013). In the presently disclosed study, EHS allowed for stable, long-term culture of a functional syncytium of hiPSC-CMs. Electrophysiological functionality was maintained for more than 200 days—EHS could be pace-captured at PCLs as short as 400 ms, and APs continued to propagate as before throughout the entirety of the preparation, although with some loss of CV that may occur as non-myocytes proliferate over time in EHS culture.

Remarkably, hiPSC-CMs cultured long-term within EHS retained their elongated morphology and aligned sarcomeres even after removal from the dECM slice, suggesting that the ECM may have durable effects on cell phenotype. Aside from cues from the ECM, additional steps may be required to optimize the structural organization and function of EHS in long-term culture.

The EHS preparation holds promise for preclinical cardiac effect testing, where accurate prediction of arrhythmia risk is essential to remove hazardous drugs from the development pipeline. Currently, drugs are tested for their ability to inhibit hERG and cause QT prolongation, a marker for risk of developing Torsades de Pointes (TdP), a tissue-level arrhythmia (Farkas and Nattel, 2010). Most studies of this kind are performed on heterologous expression systems which lack the full complement of cardiac ion channels (Fermini et al., 2016). Such assays also do not account for offsetting mechanisms from non-hERG ion channels that may render a drug safe (Redfern et al., 2003). The EHS preparation addresses these shortcomings as a functional syncytium of human CMs and allows for a multitude of mechanisms by which drugs can affect excitability, including effects on ion currents and electrical coupling.

The GRIDS assay described herein provides a new tool for evaluating drug sensitivity in the context of cellular automaticity and excitability. Changes in spontaneous beating rates are often used to evaluate drug sensitivity of hiPSC-CMs (Gilchrist et al., 2015) and can be altered by drugs that act on ICa,L or IKr (Blazeski et al., 2012). Electrophysiological measurements at variable spontaneous beat rates, however, fail to control for the rate-dependence of the various ion currents. On the other hand, GRIDS evaluates the effect of drugs during electrical pacing at different fixed rates. These periodic stimuli introduce controlled, dynamic changes into the system, and the resulting beating patterns are an integrated effect of automaticity, excitability, and refractoriness. The GRIDS map for a given drug is comprised of pace-capture responses across multiple dosing and electrical pacing regimes, and it can serve as a "fingerprint" of the drug sensitivity. The lowermost row of the GRIDS map reflects the effect of drug on spontaneous rate in the absence of electrical stimulation, while the remaining rows delineate the range of pace-capture across drug dosages. The leftmost column of the map delineates the range of pace-capture under drug-free conditions, while the remaining columns are at different drug dosages. The localization of red blocks in the upper right of the maps for E-4031 and nifedipine (monolayer only) indicates loss of capture of paced beats in the presence of high concentrations of the drug and short PCLs. Localization of blue blocks in the lower right of the maps for $BaCl_2$ indicates a higher fraction of samples with spontaneous activity as drug concentration increased, and the large area of green for chromanol 293B and nifedipine (EHS only) indicates very little response to the drug. Further, across the four drugs tested, in the GRIDS maps the regions of red or blue blocks tended to be smaller, and the region of green tended to be larger, for EHS than for monolayers, revealing that EHS are comparatively less sensitive to these drugs when evaluated for effects on their excitability and ability to capture during pacing. This suggests that EHS express relatively more of the repolarizing currents IKr and IK1, which is responsible for maintaining the resting potential in adult ventricular cells (Doss et al., 2012), than do monolayers. On the other hand, the absence of a chromanol 293B effect supports the notion that both EHS and monolayers have low levels of IKs, as has been previously described for hPSC-CMs (Ma et al., 2011). The GRIDS maps also indicate that EHS remain excitable at all PCLs and concentrations of nifedipine, whereas monolayers are unable to be pace-captured for every beat for some combinations of PCL and nifedipine concentration. Increased ICa,L in EHS would explain why for the same level of ICa,L block at a given concentration of nifedipine, EHS would retain enough residual ICa,L to remain excitable while monolayers would not. Alternatively, the excitability of EHS may be governed more by INa than by ICa,L (as in more mature ventricular tissue) compared with that of monolayers (either due to differences in ion channels or because hiPSC-CMs in EHS are less depolarized), so that block of ICa,L does not decrease excitability.

The presently disclosed GRIDS maps were able to differentiate the responses of EHS and monolayers to the panel of drugs tested even though measurements of a single electrophysiological parameter, APD prolongation, did not provide a clear snapshot of relative drug sensitivity. In both EHS and monolayers, E-4031 and $BaCl_2$ prolonged APD, chromanol 293B did not change APD, and nifedipine shortened APD. Further, differences in drug responses between EHS and monolayers were not detected with respect to APD for E-4031 (FIG. 7A,i-iii) and chromanol 293B (FIG. 7C,i-iii), but were detected for high concentrations of $BaCl_2$ and nifedipine (FIG. 7D,i-iii).

Differences in drug responses of EHS, which tend to be less sensitive but more robust in their ability to be electrically paced over a wider range of rates and drug concentrations when compared to monolayers, can be attributed to a variety of factors. One possibility is that cells in EHS are a more densely-packed, thicker syncytium that experiences a lower effective drug concentration than cells in monolayers where diffusion is not limited. Also, differences in the mechanical and biochemical environment in EHS compared to monolayers can result in differences in cell phenotype and AP morphology seen in EHS (more elongated cells with organized sarcomeres), which can affect drug responses. Additionally, EHS experience an increase in non-myocytes over time, and this modulation of cell-cell interactions in the preparation could also impact drug responses. Multicellular preparations with large areas, like EHS, will be needed in future studies to assess the risk for reentrant arrhythmias, which require room for circuitous wavefront propagation to occur. Further, EHS are tissue-like models that can be used in studies aimed at treatment discovery and at creating clinically-relevant disease models.

EHS take advantage of the complex biochemical and structural cues of the myocardial ECM to guide the alignment of CMs. Seeded hiPSC-CMs organize as multicellular, anisotropic bundles that contract the EHS and propagate APs uniformly throughout the preparation. EHS can be used for long-term culture of hiPSC-CMs to interrogate processes of cell maturation and response to drugs over time. Drug sensitivity can be evaluated for a range of concentrations and under different pacing rates using the GRIDS assay, which has revealed differences in drug sensitivity between EHS and cell monolayers. In summary, EHS are tissue-like models that can be used in long-term electrophysiology and drug studies.

Supplemental Experimental Procedures

Unless Otherwise Stated, Reagents were Acquired from Thermo Fisher Scientific, Waltham, MA Preparation of EHS Hearts obtained from slaughterhouse pigs were rinsed in distilled and deionized water to remove blood and stored overnight at −20° C. The following day, the hearts were allowed to thaw at room temperature for 1 hour. A metal 12-mm diameter punch was sterilized using 70% ethanol and used to punch out plugs of tissue from the left ventricle. Plugs were trimmed to fit into 35-mm culture dishes and stored at −80° C. until slicing, a minimum of 16 hours. Plugs were allowed to thaw in room temperature distilled water supplemented with 100 U/mL Penicillin-Streptomycin and 0.1× antibiotic-antimycotic. After thawing, plugs were blotted dry, placed in a 35-mm culture dish with the epicardium pressed against the bottom of the dish, and embedded in 4% w/v low gelling temperature agarose (Sigma-Aldrich Corp., St. Louis, MO) dissolved into distilled water with penicillin-streptomycin and antibiotic-antimycotic. The agarose was allowed to solidify at 4° C. for 15 minutes, and then the agarose disc containing the plug was removed from the culture dish and attached to the cutting stage of a vibratome (7000smz, Campden Instruments, Lafayette, IN) using cyanoacrylate glue (3M, Maplewood, MN) with the epicardium positioned at the top of the plug. The plug was sectioned into 300 μm-thick slices parallel to the epicardium using a ceramic blade oscillating at a frequency of 100 Hz with an amplitude of 1 mm and advancing at a speed of 0.01 to 0.03 mm/second. The cutting solution in which the plug was immersed (phosphate buffered saline (PBS) supplemented with antibiotics) was kept at 4-8° C. during slicing. Slices were stored in PBS supplemented with antibiotics at 4° C. overnight.

Slices were decellularized using a procedure modified from Ott et al., 2008. All detergents for decellularization were diluted in distilled water supplemented with antibiotics. PBS also was supplemented with the same antibiotics. Slices were each placed in a well of a 12-well plate, and 1 mL of each of the decellularization solutions was added to each well. The plate was placed on a rotator (Orbit 1000 Digital Shaker, Labnet International Inc., Edison, NJ) and agitated 180 rpm in the presence of the following solutions: 1% sodium dodecyl sulfate (SDS) for 3 hours (replaced with fresh solution after 1.5 hours), water for 15 minutes, 1% Triton-X 100 (Sigma-Aldrich Corp.) for 7 minutes, and PBS for 45 minutes (replaced with fresh solution every 15 minutes). Samples were left in PBS on rotator at 160 rpm overnight to rinse out any remaining detergents.

Plastic 12-mm coverslips were immersed in 70% ethanol and wiped dry. After an overnight wash in PBS, slices were carefully handled with forceps, spread over the coverslips and wrapped around the edges of the coverslips. Slices attached to the coverslips were placed into wells of a 24-well plate, immersed in PBS with antibiotics, and stored at 4° C. until seeding (up to 2 weeks).

hiPSC Differentiation and Culture

Wild type and LQT2 hiPSCs were plated into wells of 6-well plates coated with 1:200 Geltrex:DMEM/F-12. For the first 22 hours, hiPSCs were maintained in Essential 8 medium (E8) with 10 μM Y-27632 dihydrochloride (Tocris Bioscience, Bristol, UK). Afterwards, hiPSCs were rinsed with DMEM/F-12 and fed with E8 medium every day. On the fourth day, when cells had reached about 80% confluence, the medium was replaced with RPMI 1640 supplemented with B-27, minus insulin and 6 μM CHIR-99021 (Selleck Chemicals, Houston, TX) to initiate differentiation (d0 of differentiation). Over the course of the next week, medium was changed as follows: RPMI 1640 with B-27 without insulin (B-27 minus) on d2, B-27 minus and 5 μM IWR-1 (Sigma-Aldrich Corp.) on d3, B-27 minus on d5 and d7, and RPMI 1640 with B-27 with insulin (B-27 plus) on d9 and every other day afterwards. Spontaneous beating in the monolayers was observed starting at d7 to d10. On d10 to d12, the hiPSC-CM monolayers were washed with 0.5 mM EDTA (Mediatech, Inc., Manassas, VA) and then incubated in EDTA for 5 minutes at 37° C. Afterwards, the EDTA was aspirated off, and 0.05% Trypsin-EDTA was added for 3 minutes at 37° C. Cells were triturated before Defined Trypsin Inhibitor was added to stop the digestion. The resultant suspension was centrifuged at 200 g for 5 minutes (Centrifuge 5702, Eppendorf AG, Hamburg, Germany). After aspirating off the supernatant, the cell pellet was resuspended in B-27 plus. The PBS was removed from dECM slices, and the suspension of hiPSC-CMs was pipetted on top of the slices at a density of 0.8 to 1.3 million cells per $cm^2$. Slices were maintained in culture for 16 to 190 days, and the B-27 plus medium was replaced every other day for the duration of culture.

Imaging of Extracellular Matrix and EHS dECM slices or EHS were fixed in 4% paraformaldehyde solution (Affymetrix, Inc., Cleveland, OH) for 10 minutes and rinsed twice with PBS. Samples were stored in PBS at 4° C. until immunostaining. To immunostain for ECM proteins, slices were immersed in Target Retrieval Solution (Dako North America, Inc., Carpinteria, CA) for 20 minutes in a steamer.

Samples were subsequently rinsed in distilled, deionized water for 5 minutes, blocked with 10% peroxide solution in water (Sigma-Aldrich Corp.) for 10 minutes, and rinsed twice for 5 minutes each time with Dulbecco's Phosphate Buffered Saline (DPBS). Samples were incubated in primary antibodies against collagen I (C2456, Sigma-Aldrich Corp.), collagen III (ab7778, Abcam, Cambridge, MA), and laminin (L9393, Sigma-Aldrich Corp.). The next day, slices were washed three times for 5 minutes each with TBS-T (0.05% Tween 20, Sigma-Aldrich Corp.) in Tris Buffered Saline (TBS, Quality Biological, Gaithersburg, MD) and incubated in secondary antibodies (Invitrogen, Waltham, MA) for 45 minutes at room temperature. EHS were shielded from exposure to light and washed in three rounds of TBS-T for 5 minutes each round.

Afterwards, samples were mounted onto slides, a drop of Prolong Gold Antifade Mountant was added onto the slices, and a glass slide was placed on top. Samples were left to dry for a minimum of 24 hours before acquiring images using a confocal microscope (LSM 510 Meta, Zeiss, Oberkochen, Germany). Fibrillar collagen in unstained dECM slices was also imaged by second harmonic generation (SHG) using a multiphoton microscope (710NLO, Zeiss) with excitation at 880 nm, and emission acceptance at 415-450 nm.

To immunostain for cellular proteins, EHS were permeabilized with cold 0.5% Triton-X100 (Sigma-Aldrich Corp.) in PBS for 20 minutes, followed by blocking with 10% goat serum (Life Technologies, Carlsbad, CA) for 1 hour at room temperature. Primary antibodies against cardiac troponin I (T8665-13F, United States Biological, Pittsburgh, PA), α-actinin (A7811,Sigma-Aldrich Corp.), connexin 43 (C6219, Sigma-Aldrich Corp.), or vimentin (M0725, Dako North America, Inc.) in antibody diluent (Dako North America, Inc.) were added overnight at 4° C. The next day, EHS were washed with TBS-T as described above. Afterwards, samples were stained with 4',6-Diamidino-2 Phenylindole, Dihydrochloride (DAPI) for 25 minutes at room temperature. Samples were subjected to three more rounds of TBS-T washing before the addition of a drop of Prolong Gold Antifade Mountant and a glass slide on top of each sample.

Alternatively, some samples were permeabilized as previously described and stained with Alexa Fluor 488 Phalloidin and DAPI at room temperature for 25 minutes. Samples were washed in TBS-T and mounted for imaging as described above. Images of stained samples were acquired using a confocal microscope (LSM 510 Meta, Zeiss). To prepare samples for transmission electron microscopy, EHS were fixed in 2.5% glutaraldehyde and 3 mM $MgCl_2$ in 0.1 M sodium cacodylate buffer (pH 7.2) overnight at 4° C. Samples were subsequently rinsed three times (15 minutes per rinse) in a 0.1 M sodium cacodylate buffer supplemented with 3 mM $MgCl_2$ and 3% sucrose, shielded from light, and left for one hour in a solution of 1% osmium tetroxide in 3 mM $MgCl_2$ and 0.1 M sodium cacodylate buffer. After undergoing two rounds of rinsing with water for 5 minutes each, the samples were stained in 2% aqueous uranyl acetate in the dark for 1 hour. Samples were then dehydrated in a graded series of ethanol washes (30%, 50%, 70%, 90%, and three washes of 100% ethanol), followed by two washes with propylene oxide (for 5 minutes each) and an overnight incubation in 1:1 propylene oxide:epon. The next day, samples were incubated in epon with catalyst three times for 2 hours each at room temperature and for 2 days at 60° C. Samples were examined using a transmission electron microscope (Phillips/FEI BioTwin CM120 TEM, Hillsboro, OR).

1.7.4. Calculation of Collagen Fiber Orientation

SHG images were acquired of three types of decellularized slices (dECM slices) after decellularizing: fresh slices (native slices from sections of fresh plugs prepared right after the hearts were acquired that were decellularized), frozen slices (fresh slices that were stored at −80° C. for over 48 hours), and frozen plus (fresh plugs that were stored at −80° C. for over 48 hours, thawed, and subsequently sectioned). Both fresh and frozen plugs were acquired from the same hearts, and fresh and frozen slices were derived from adjacent sections of the same plug. SHG z-stack images had an area of 1.875 $mm^2$ and were processed in MATLAB to quantify fiber orientation and fiber degree of alignment. After compressing z-stack images in ImageJ using a maximum intensity z-axis projection, each compressed image was converted to an RGB image using ImageJ and segmented in MATLAB. SHG images were then segmented into 6889 subregions. The sectioning frame originated at the top left corner of the image and continuously shifted to the right or downwards by 0.0133 mm to create a new subregion with an area of 0.071 $mm^2$. The absolute logarithmic magnitude of the 2D Fast-Fourier transform (2D-FFT) was calculated for each subregion in the segmented image. The direct current frequency was shifted to the center of the 2D-FFT plot, and the magnitude of the 2D-FFT was normalized so that it had a magnitude of 1. Since the 2D-FFT is symmetric, only half of it was used in the analysis. The angle of orientation from the horizontal axis of each coordinate in the 2D-FFT was calculated by converting from Cartesian to polar coordinates.

The radial sum of the 2D-FFT, normalized to the number of pixels along each radius, was plotted as a function of the orientation for each subregion. The orientation of the maximum 2DFFT sum determined the angle perpendicular to the fiber orientation in that subregion. The mean and standard deviation of the fiber orientation were calculated for all subregions in each image. Mean values of fiber orientation were plotted for 8 slices within each group. The fiber degree of alignment was calculated as the maximum 2D-FFT sum divided by the total sum of the 2D-FFTs of all subregions within an image.

Calculation of Nuclear Elongation and Alignment

Time-matched EHS and monolayers were immunostained with DAPI and imaged using a confocal microscope, as described above. Images of nuclei were thresholded above a baseline noise level and segmented, removing overlapping areas as necessary, by using a previously described method (Plissiti et al., 2014) with some modifications. A recursive search for concavity points was performed; when a concavity point was found, the outline between it and the convex hull was searched for more concavities. Further, the case where non-adjoining sections of an outline are part of the same nucleus was permitted. An ellipse was fitted to each nucleus using a method previously described (Fitzgibbon et al., 1999). The nuclear elongation ratio, mean angular orientation, and standard deviation of the angular orientations were calculated, as previously described (Bray et al., 2010).

Flow Cytometry Analysis

Flow cytometry analysis was performed on d17 (prior to monolayer seeding), and on monolayers and EHS that had been seeded at d17 and cultured for 61 days (d68). Monolayers and d17 cells were washed with 5 mM EDTA and subsequently incubated in 5 mM EDTA at 37° C. for 5 minutes. The EDTA solution was aspirated off and replaced with 0.05% Trypsin-EDTA for 4-6 minutes at 37° C., until the cells easily detached from the bottom of the wells when the culture dish was agitated. The Trypsin-EDTA solution containing cells was neutralized using Defined Trypsin Inhibitor, and the cells were centrifuged at 200 g for 5 minutes before fixation.

EHS were unhooked from their underlying plastic coverslip, transferred to a 12-well plate and rinsed with DPBS containing calcium and magnesium (DPBS+/+). After removing the DPBS, EHS were incubated in 10 mg/mL of collagenase IV with 10% fetal bovine serum in DPBS+/+ and 50 μg/mL of DNAse I in 0.15 M NaCl (Sigma-Aldrich Corp.) for 30 minutes on a shaker at 37° C. The collagenase and DNAse solution were subsequently removed, and the EHS were rinsed twice with PBS (without calcium or magnesium). After removing the PBS, EHS were incubated in 0.05% Trypsin-EDTA for 5 minutes on a shaker at 37° C. and broken up by pipetting up and down. The Trypsin-EDTA solution containing the recovered cells was neutralized and centrifuged as described above prior to fixation.

Dissociated cells were fixed in 4% paraformaldehyde (Affymetrix) for 10 min at room temperature. Cells were then simultaneously and permeabilized and blocked in PBS containing 0.1% BSA (Sigma-Aldrich Corp.), 5% goat serum, and 0.1% Triton-X 100 (Sigma-Aldrich Corp.) for 30 min. Cells were incubated with mouse anti-cTnT antibody diluted 1:200 in FACS buffer (PBS with 0.1% BSA and 0.1% Triton-X 100) for 1 hr at 4° C., washed three times with FACS buffer, and incubated with anti-mouse Alexa Fluor® 488 antibody in FACS buffer (1:200, Invitrogen) for 30 min at 22° C. in the dark. After washing and re-suspending in PBS with 0.1% BSA, cells were strained through a 30 μm filter and run on a FACSCalibur cytometer (BD Biosciences, Woburn, MA). Secondary controls consisted of cells incubated only with antimouse Alexa Fluor® 488 secondary antibody. Single cells were identified and gated based on their forward and side scatter, and cardiomyocytes were gated based on their cTnT expression.

Data were analyzed using FlowJo X Software. Histogram counts were extracted by gating on unstained cells and cells stained only with secondary antibody control (to remove autofluorescence and background nonspecific secondary staining).

Contraction Measurements

Tyrode's solution was prepared by combining 1.8 mM $CaCl_2$, 5 mM glucose, 5 mM HEPES, 1 mM $MgCl_2$, 5.4 mM KCl, 135 mM NaCl, and 0.33 mM $NaH_2PO_4$ in $ddH_2O$ and adding NaOH to raise the pH to 7.4 (all chemicals from Sigma-Aldrich Corp.). EHS were placed in a 35-mm dish filled with Tyrode's solution and set on a stage heated to 31±0.1° C. (Warner Instruments, Hamden, CT). A section of each EHS was unhooked and allowed to move freely throughout the duration of the experiment. The EHS were allowed to equilibrate in Tyrode's for 5 minutes before the start of pacing with a point electrode. Each sample was paced for 1 minute at each of 3 cycle lengths (1000 ms, 666 ms, 500 ms), while the freely moving region was kept approximately vertical in the field of view and imaged at 4× magnification using a CCD camera (Swiftcam, Swift, Schertz, TX) at a rate of 14-17 fps with 320×256 pixel resolution. Samples also were imaged during pacing at 666 ms after the application of 1 μM isoproterenol (Sigma-Aldrich Corp.) for 2 minutes and after washout of the drug for 2 minutes. A pacing cycle length shorter than 1000 ms was applied in the presence of isoproterenol to overcome the increase in spontaneous rate in response to the drug. Custom MATLAB scripts were used to segment the images by applying a user-defined threshold to assign each pixel in the image as either belonging to the EHS, which was darker, or the background, which was lighter. From this, the area of EHS was calculated in each image. The change in area from a fully relaxed state (reference frame, designated as 100% EHS area) was determined for each frame in the time series. The minimum area (maximum change in area) was averaged over time (multiple cycles of contraction) and relaxation for each pacing condition. The change in area in the presence of isoproterenol and after washout was compared to the change in area prior to the application of drug for each EHS.

Electrophysiological Studies

EHS were stained with 10 μM of the voltage-sensitive dye di-4-ANEPPS (Sigma-Aldrich Corp.) in Tyrode's solution for 10 minutes at 37° C. Afterwards, EHS were rinsed twice with Tyrode's and placed in a 35-mm dish filled with Tyrode's and 10 μM of the contraction inhibitor blebbistatin (Sigma-Aldrich Corp.). This dish was set on a stage heated to 37° C. and allowed to equilibrate for at least 5 minutes. Samples were point paced with at least 30 stimulus pulses at a range of cycle lengths, starting from 2000 ms and decreasing until the they lost capture. EHS were optically mapped during pacing using a 100×100 pixel CMOS camera (MiCAM Ultima-L, SciMedia, Costa Mesa, CA).

During drug studies, recordings at a range of pacing rates were taken at baseline (prior to the addition of drug) before replacing the solution in the dish with Tyrode's supplemented with blebbistatin and the lowest dose of drug studied. The sample was paced at the same range of rates and mapped 7 minutes after the addition of drug. Afterwards, the bath solution was replaced with Tyrode's with blebbistatin and the next lowest drug dose and the procedure repeated. This method was applied for all doses of each drug and, except where noted in the figures, only one drug was tested per sample. In these studies, we superfused EHS or monolayers with the following drugs: E-4031 (Tocris Bioscience), $BaCl_2$ (Sigma-Aldrich Corp.), Chromanol 293B (Tocris Bioscience), Nifedipine (Tocris Bioscience), Bay K 8644 (Tocris Bioscience), and Cromakalim (Sigma-Aldrich Corp.).

Optical mapping data was analyzed using custom MATLAB scripts. Recordings at each pixel were de-noised using a previously described method (Little and Jones, 2010) to regulate total signal variance and convolved with a 5×5 spatial Gaussian filter. Activation times were defined as the maximum of the derivative of membrane potential (dV/dt), which was calculated as previously described (Chartrand, 2011). Histograms of local conduction velocities for each EHS were fitted to a Gaussian curve and the mean of the curve was defined as the average conduction velocity (CV). To determine longitudinal and transverse CVs, a bimodal Gaussian curve was fitted to the local CVs. Action potential durations at 30 and 80 percent repolarization (APD30 and APD80) were determined for all local traces over the recording region for each EHS and fit with Gaussian curves to determine the mean value for each EHS, as described for CV measurements. For drug studies, average APD and CV measurements for each dose were normalized by average APD and CV measurements at baseline (without the drug).

Quantitative RT-PCR mRNA was isolated from EHS (d69) and monolayers (d22) using the following procedure: incubation in TRIzol Reagent for 5 minutes at room temperature, incubation in chloroform for 3 minutes, centrifugation at 12,000 g for 15 minutes at 4° C., collection of colorless phase that separated at the top of the centrifuged sample, addition of isopropyl alcohol and incubation at room temperature for 10 minutes, centrifugation at 12,000 g for 10 minutes at 4° C., solubilization of RNA pellet in 75% ethanol, centrifugation at 7,500 g for 5 minutes at 4° C., air drying of sample, and resuspension of the RNA pellet in DEPC-treated water. mRNA from two EHS were combined for each EHS replicate.

Reverse transcription was performed to create cDNA with the PCR Master Mix kit, using the MyGo Mini PCR system (IT-IS Life Science Ltd., Republic of Ireland). RT-PCR was performed on each target in triplicate, using the following primers:

| Gene Target | Associated Protein | | Primer |
|---|---|---|---|
| CACNA1C | L-type calcium channel | Forward<br>Reverse | CACGGCTTCCTCGAATCTTG<br>CTGTGGAGATGGTCGCATTG |

-continued

| Gene Target | Associated Protein | | Primer |
|---|---|---|---|
| KCNH2 | Voltage-gated potassium channel | Forward | AGGAGCGAACCCACAATGTC |
| | | Reverse | AGGTGGTGCGGAAGTTGATG |
| TNNI1 | Troponin I, slow skeletal type | Forward | GGTGGATGAGGAGCGATACG |
| | | Reverse | CAGGCTGGAGGGAAGAAGTG |
| TNNI3 | Troponin I, cardiac | Forward | CCAACTACCGCGCTTATGCC |
| | | Reverse | CCTTCTCGGTGTCCTCCTTC |

The PCR program run for each sample consisted of 120 seconds hold at 95° C., 40 cycles of amplification that alternated between 90° C. and 65° C., 10 seconds pre-melt hold at 95° C., and a melting step that increased from 60° C. to 97° C. at 0.1° C./second. CT values were obtained using MyGo Mini PCR Software (IT-IS Life Science Ltd.) and CT was calculated for each gene of interest (GOI) in EHS to determine fold change over transcript levels expressed monolayers according to the formula:

$$\Delta\Delta C_T = C^{EHS}{}_{T,GOI} - C^{EHS}{}_{T,ACTN2} - C^{Mn}{}_{T,GOI} + C^{Mn}{}_{T,ACTN2}$$

where $C^{EHS}{}_{T,GOI}$ refers to $C_T$ of EHS for the GOI, $C^{EHS}{}_{T,ACTN2}$ refers to $C_T$ of EHS for ACTN2 (α-actinin, which was used as a normalizing gene), $C^{Mn}{}_{T,GOI}$ refers to $C_T$ of monolayers for the GOI, and $C^{Mn}{}_{T,ACTN2}$ refers to $C_T$ of monolayers for ACTN2.

Statistics

All data are presented as mean±SD. Measurements of nuclear elongation were log transformed and reported as the interval of the log-transformed mean±SD after inverse transformation into linear space (Bland and Altman, 1996). For contraction experiments, a one-tailed Wilcoxon test was used to determine statistically significant differences from 1 for isoproterenol-treated and washout groups. For studies on rate-dependence of contraction, a two-tailed Wilcoxon test was used to determine statistically significant differences from 1 for groups paced at 500 ms and 1000 ms cycle lengths. A two-tailed Wilcoxon test was also used for statistical significance between APD measurements for WT and LQT2 EHS. Paired, unequal variance, two-tailed t-tests were performed for all other drug studies and unpaired, unequal variance, two-tailed t-tests were performed for optical mapping studies not involving drugs, studies comparing d62-82 EHS to d201 EHS, and for orientation analysis of fresh slices, frozen slices, and frozen plugs.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Akhyari, P., Aubin, H., Gwanmesia, P., Barth, M., Hoffmann, S., Huelsmann, J., Preuss, K., and Lichtenberg, A. (2011). The Quest for an Optimized Protocol for Whole-Heart Decellularization: A Comparison of Three Popular and a Novel Decellularization Technique and Their Diverse Effects on Crucial Extracellular Matrix Qualities. Tissue Eng. Part C Methods 17, 915-926.

Arrowsmith, J. & Miller, P. Trial watch: phase II and phase III attrition rates 2011-2012. Nature reviews. Drug discovery 12, 569 (2013).

Badylak, S. F., Taylor, D., and Uygun, K. (2010). Whole Organ Tissue Engineering: Decellularization and Recellularization of Three-Dimensional Matrix Scaffolds. Annu. Rev. Biomed. Eng. 13, 110301095218061.

Baharvand, H., Azarnia, M., Parivar, K., and Ashtiani, S. K. (2005). The effect of extracellular matrix on embryonic stem cell-derived cardiomyocytes. J. Mol. Cell. Cardiol. 38, 495-503.

Bland, J. M., and Altman, D. G. (1996). Transformations, means, and confidence intervals. BMJ 312, 1079.

Blazeski, A., Zhu, R., Hunter, D. W., Weinberg, S. H., Zambidis, E. T., and Tung, L. (2012). Cardiomyocytes derived from human induced pluripotent stem cells as models for normal and diseased cardiac electrophysiology and contractility. Prog. Biophys. Mol. Biol. 110, 166-177.

Blazeski, A., Kostecki, G. M., and Tung, L. (2015). Engineered heart slices for electrophysiological and contractile studies. Biomaterials 55, 119-128.

Boheler, K. R., Bhattacharya, S., Kropp, E. M., Chuppa, S., Riordon, D. R., Bausch-Fluck, D., Burridge, P. W., Wu, J. C., Wersto, R. P., Chan, G. C. F., et al. (2014). A human pluripotent stem cell surface N-glycoproteome resource reveals markers, extracellular epitopes, and drug targets. Stem Cell Reports 3, 185-203.

Bray, M.-A. P., Adams, W. J., Geisse, N. a, Feinberg, A. W., Sheehy, S. P., and Parker, K. K. (2010). Nuclear morphology and deformation in engineered cardiac myocytes and tissues. Biomaterials 31, 5143-5150.

Burridge, P. W., Keller, G., Gold, J. D., and Wu, J. C. (2012). Production of De Novo Cardiomyocytes: Human Pluripotent Stem Cell Differentiation and Direct Reprogramming. Stem Cell 10, 16-28.

Carvalho, J. L. (2012). Characterization of decellularized heart matrices as biomaterials for regular and whole organ tissue engineering and initial in-vitro recellularization with iPS cells. J. Tissue Sci. Eng. S11.

Chartrand, R. (2011). Numerical differentiation of noisy, nonsmooth data. ISRN Appl. Math. 2011, 1-11.

Colan, S. D., Borow, K. M., and Neumann, A. (1984). Left ventricular end-systolic wall stress-velocity of fiber shortening relation: A load-independent index of myocardial contractility. J. Am. Coll. Cardiol. 4, 715-724. de Diego, C., Chen, F., Xie, Y., Pai, R. K., Slavin, L., Parker, J., Lamp, S. T., Qu, Z., Weiss, J. N., and Valderrábano, M. (2011). Anisotropic conduction block and reentry in neonatal rat ventricular myocyte monolayers. Am. J. Physiol. Heart Circ. Physiol. 300, H271-H278.

Doss, M. X., Di Diego, J. M., Goodrow, R. J., Wu, Y., Cordeiro, J. M., Nesterenko, V. V, Barajas-Martinez, H., Hu, D., Urrutia, J., Desai, M., et al. (2012). Maximum diastolic potential of human induced pluripotent stem cell-derived cardiomyocytes depends critically on I(Kr). PLoS One 7, e40288.
Duan, Y., Liu, Z., O'Neill, J., Wan, L. Q., Freytes, D. O., and Vunjak-Novakovic, G. (2011). Hybrid gel composed of native heart matrix and collagen induces cardiac differentiation of human embryonic stem cells without supplemental growth factors. J. Cardiovasc. Transl. Res. 4, 605-615.
Durrer, D., van Dam, R. T., Freud, G. E., Janse, M. J., Meijler, F. L., and Arzbaecher, R. C. (1970). Total excitation of the isolated human heart. Circulation 41, 899-912.
Farkas, A. S., and Nattel, S. (2010). Minimizing repolarization-Related proarrhythmic risk in drug development and clinical practice. Drugs 70, 573-603.
Feaster, T. K., Cadar, A. G., Wang, L., Williams, C. H., Chun, Y. W., Hempel, J. E., Bloodworth, N., Merryman, W. D., Lim, C. C., Wu, J. C., et al. (2015). Matrigel Mattress: A Method for the Generation of Single Contracting Human-Induced Pluripotent Stem Cell-Derived Cardiomyocytes. Circ. Res. 117, 995-1000.
Fermini, B., Hancox, J. C., Abi-gerges, N., Bridgland-taylor, M., Chaudhary, K. W., Colatsky, T., Correll, K., Crumb, W., Damiano, B., Erdemli, G., et al. (2016). A New Perspective in the Field of Cardiac Safety Testing through the Comprehensive In Vitro Proarrhythmia Assay Paradigm.
Fitzgibbon, A., Pilu, M., and Fisher, R. B. (1999). Direct least square fitting of ellipses. IEEE Trans. Pattern Anal. Mach. Intell. 21, 476-480.
French, K. M., Boopathy, A. V., Dequach, J. A., Chingozha, L., Lu, H., Christman, K. L., and Davis, M. E. (2012). A naturally derived cardiac extracellular matrix enhances cardiac progenitor cell behavior in vitro. Acta Biomater. 8, 4357-4364.
Gershlak, J. R., Resnikoff, J. I. N., Sullivan, K. E., Williams, C., Wang, R. M., and Black, L. D. (2013). Mesenchymal stem cells ability to generate traction stress in response to substrate stiffness is modulated by the changing extracellular matrix composition of the heart during development. Biochem. Biophys. Res. Commun. 439, 161-166.
Gilchrist, K. H., Lewis, G. F., Gay, E. A., Sellgren, K. L., and Grego, S. (2015). High-throughput cardiac safety evaluation and multi-parameter arrhythmia profiling of cardiomyocytes using microelectrode arrays. Toxicol. Appl. Pharmacol. 288, 249-257.
Guyette, J. P., Charest, J. M., Mills, R. W., Jank, B. J., Moser, P. T., Gilpin, S. E., Gershlak, J. R., Okamoto, T., Gonzalez, G., Milan, D. J., et al. (2016). Bioengineering human myocardium on native extracellular matrix. Circ. Res. 118, 56-72.
Herron, T. J., Da Rocha, A. M., Campbell, K. F., Ponce-Balbuena, D., Willis, B. C., Guerrero-Serna, G., Liu, Q., Klos, M., Musa, H., Zarzoso, M., et al. (2016). Extracellular matrix-mediated maturation of human pluripotent stem cell-derived cardiac monolayer structure and electrophysiological function. Circ. Arrhythmia Electrophysiol. 9.
Kamakura, T., Makiyama, T., Sasaki, K., Yoshida, Y., Wuriyanghai, Y., Chen, J., Hattori, T., Ohno, S., Kita, T., Horie, M., et al. (2013). Ultrastructural Maturation of Human-Induced Pluripotent Stem Cell-Derived Cardiomyocytes in a Long-Term Culture. Circ. J. 77, 1307-1314.
Li, X., Zhang, R., Zhao, B., Lossin, C. & Cao, Z. Cardiotoxicity screening: a review of rapid-throughput in vitro approaches. Arch. Toxicol. 90, 1803-1816 (2016).
Liau, B., Christoforou, N., Leong, K. W., and Bursac, N. (2011). Pluripotent stem cell-derived cardiac tissue patch with advanced structure and function. Biomaterials 32, 9180-9187.
Little, M. A., and Jones, N. S. (2010). Sparse Bayesian step-filtering for high-throughput analysis of molecular machine dynamics. In 2010 IEEE International Conference on Acoustics, Speech and Signal Processing, pp. 4162-4165.
Lu, T.-Y., Lin, B., Kim, J., Sullivan, M., Tobita, K., Salama, G., and Yang, L. (2013). Repopulation of decellularized mouse heart with human induced pluripotent stem cell-derived cardiovascular progenitor cells. Nat. Commun. 4, 2307.
Lundy, S. D., Zhu, W.-Z., Regnier, M., and Laflamme, M. A. (2013). Structural and functional maturation of cardiomyocytes derived from human pluripotent stem cells. Stem Cells Dev. 22, 1991-2002.
Ma, J., Guo, L., Fiene, S. J., Anson, B. D., Thomson, J. A., Kamp, T. J., Kolaja, K. L., Swanson, B. J., January, C. T., Kl, K., et al. (2011). High purity human-induced pluripotent stem cell-derived cardiomyocytes: electrophysiological properties of action potentials and ionic currents. Am J Physiol Hear. Circ Physiol 301, 2006-2017.
Ma, Z., Koo, S., Finnegan, M. a, Loskill, P., Huebsch, N., Marks, N. C., Conklin, B. R., Grigoropoulos, C. P., and Healy, K. E. (2014). Three-dimensional filamentous human diseased cardiac tissue model. Biomaterials 35, 1367-1377.
Macadangdang, J., Guan, X., Smith, A. S. T., Lucero, R., Czerniecki, S., Childers, M. K., Mack, D. L., and Kim, D.-H. (2015). Nanopatterned Human iPSC-based Model of a Dystrophin-Null Cardiomyopathic Phenotype. Cell. Mol. Bioeng. 8, 320-332.
Magdy, T., Schuldt, A. J. T., Wu, J. C., Bernstein, D. & Burridge, P. W. Human Induced Pluripotent Stem Cell (hiPSC)-Derived Cells to Assess Drug Cardiotoxicity: Opportunities and Problems. Annu. Rev. Pharmacol. Toxicol 582221, 1-22 (2018).
Mannhardt, I., Breckwoldt, K., Letuffe-Brenière, D., Schaaf, S., Schulz, H., Neuber, C., Benzin, A., Werner, T., Eder, A., Schulze, T., Klampe, B., Christ, T., Hirt, M. N., Huebner, N., Moretti, A., Eschenhagen, T. & Hansen, A. Human Engineered Heart Tissue: Analysis of Contractile Force. Stem cell reports 7, 29-42 (2016).
Matsuura, K., Wada, M., Shimizu, T., Haraguchi, Y., Sato, F., Sugiyama, K., Konishi, K., Shiba, Y., Ichikawa, H., Tachibana, A., et al. (2012). Creation of human cardiac cell sheets using pluripotent stem cells. Biochem. Biophys. Res. Commun. 425, 321-327.
Mitchell, L. B., Schroeder, J. S., and Mason, J. W. (1982). Comparative clinical electrophysiologic effects of diltiazem, verapamil and nifedipine: a review. Am. J. Cardiol. 49, 629-635.
Nakayama, K. H., Hou, L., and Huang, N. F. (2014). Role of extracellular matrix signaling cues in modulating cell fate commitment for cardiovascular tissue engineering. Adv. Healthc. Mater. 3, 628-641.
Ng, S. L. J., Narayanan, K., Gao, S., and Wan, A. C. a (2011). Lineage restricted progenitors for the repopulation of decellularized heart. Biomaterials 32, 7571-7580.
Nunes, S. S., Miklas, J. W., Liu, J., Aschar-Sobbi, R., Xiao, Y., Zhang, B., Jiang, J., Massé, S., Gagliardi, M., Hsieh, A., Thavandiran, N., Laflamme, M. a, Nanthakumar, K., Gross, G. J., Backx, P. H., Keller, G. & Radisic, M. Biowire: a platform for maturation of human pluripotent stem cell-derived cardiomyocytes. Nat. Methods 10, 781-7 (2013).

Oberwallner, B., Brodarac, A., Anić, P., Sarić, T., Wassilew, K., Neef, K., Choi, Y.-H., and Stamm, C. (2014). Human cardiac extracellular matrix supports myocardial lineage commitment of pluripotent stem cells. Eur. J. Cardiothorac. Surg. 1-10.

Ott, H. C., Matthiesen, T. S., Goh, S.-K., Black, L. D., Kren, S. M., Netoff, T. I., and Taylor, D. a (2008). Perfusion-decellularized matrix: using nature's platform to engineer a bioartificial heart. Nat. Med. 14, 213-221.

Peters, N. S., and Wit, A. L. (1998). Myocardial architecture and ventricular arrhythmogenesis. Circulation 97, 1746-1754.

Plissiti, M. E., Louka, E., and Nikou, C. (2014). Splitting of overlapping nuclei guided by robust combinations of concavity points. In SPIE Medical Imaging 2014, S. Ourselin, and M. A. Styner, eds. p. 903431.

Rao, C., Prodromakis, T., Kolker, L., Chaudhry, U. A. R., Trantidou, T., Sridhar, A., Weekes, C., Camelliti, P., Harding, S. E., Darzi, A., et al. (2013). The effect of microgrooved culture substrates on calcium cycling of cardiac myocytes derived from human induced pluripotent stem cells. Biomaterials 34, 2399-2411.

Ravens, U., and Wettwer, E. (1998). Electrophysiological aspects of changes in heart rate. Basic Res. Cardiol. 93 Suppl 1, 60-65.

Redfern, W. S., Carlsson, L., Davis, A. S., Lynch, W. G., MacKenzie, I., Palethorpe, S., Siegl, P. K. S., Strang, I., Sullivan, A. T., Wallis, R., et al. (2003). Relationships between preclinical cardiac electrophysiology, clinical QT interval prolongation and torsade de pointes for a broad range of drugs: evidence for a provisional safety margin in drug development. Cardiovasc. Res. 58, 32-45.

Rehnelt, S., Malan, D., Juhasz, K., Wolters, B., Doerr, L., Beckler, M., Kettenhofen, R., Bohlen, H., Bruegmann, T. & Sasse, P. Frequency-dependent multi-well cardiotoxicity screening enabled by optogenetic stimulation. Int. J. Mol. Sci. 18, (2017).

Ronaldson-Bouchard, K., Ma, S. P., Yeager, K., Chen, T., Song, L., Sirabella, D., Morikawa, K., Teles, D., Yazawa, M., and Vunjak-Novakovic, G. (2018). Advanced maturation of human cardiac tissue grown from pluripotent stem cells. Nature 556, 239-243.

Spencer, C. I., Baba, S., Nakamura, K., Hua, E. a, Sears, M. a F., Fu, C.-C., Zhang, J., Balijepalli, S., Tomoda, K., Hayashi, Y., et al. (2014). Calcium transients closely reflect prolonged action potentials in iPSC models of inherited cardiac arrhythmia. Stem Cell Reports 3, 269-281.

Tester, D. J., and Ackerman, M. J. (2014). Genetics of long QT syndrome. Methodist Debakey Cardiovasc. J. 10, 29-33.

Tzatzalos, E., Abilez, O. J., Shukla, P., and Wu, J. C. (2015). Engineered heart tissues and induced pluripotent stem cells: Macro- and microstructures for disease modeling, drug screening, and translational studies. Adv. Drug Deliv. Rev. 96, 234-244.

Veeraraghavan, R., Gourdie, R. G., and Poelzing, S. (2014). Mechanisms of cardiac conduction: a history of revisions. AJP Hear. Circ. Physiol. 306, H619-H627.

Wang, G., McCain, M. L., Yang, L., He, A., Pasqualini, F. S., Agarwal, A., Yuan, H., Jiang, D., Zhang, D., Zangi, L., et al. (2014). Modeling the mitochondrial cardiomyopathy of Barth syndrome with induced pluripotent stem cell and heart-on-chip technologies. Nat. Med. 20, 616-623.

Wang, J., Chen, A., Lieu, D. K., Karakikes, I., Chen, G., Keung, W., Chan, C. W., Hajjar, R. J., Costa, K. D., Khine, M., et al. (2013). Effect of engineered anisotropy on the susceptibility of human pluripotent stem cell-derived ventricular cardiomyocytes to arrhythmias. Biomaterials 34, 8878-8886.

Wang, Y., Li, Z. C., Zhang, P., Poon, E., Kong, C. W., Boheler, K. R., Huang, Y., Li, R. A., and Yao, X. (2015). Nitric Oxide-cGMP-PKG Pathway Acts on Orail to Inhibit the Hypertrophy of Human Embryonic Stem Cell-Derived Cardiomyocytes. Stem Cells 33, 2973-2984.

Wanjare, M., Hou, L., Nakayama, K. H., Kim, J. J., Mezak, N. P., Abilez, O. J., Tzatzalos, E., Wu, J. C., and Huang, N. F. (2017). Anisotropic microfibrous scaffolds enhance the organization and function of cardiomyocytes derived from induced pluripotent stem cells. Biomater. Sci. 5, 1567-1578.

Wood, A. J. J., and Roden, D. M. (2004). Drug-induced prolongation of the QT interval. N. Engl. J. Med. 350, 1013-1022.

Yue, A. M., Franz, M. R., Roberts, P. R., and Morgan, J. M. (2005). Global endocardial electrical restitution in human right and left ventricles determined by noncontact mapping. J. Am. Coll. Cardiol. 46, 1067-1075.

Zhang, D., Shadrin, I. Y., Lam, J., Xian, H. Q., Snodgrass, H. R., and Bursac, N. (2013). Tissue engineered cardiac patch for advanced functional maturation of human ESC-derived cardiomyocytes. Biomaterials 34, 5813-5820.

Zhang, J., Klos, M., Wilson, G. F., Herman, A. M., Lian, X., Raval, K. K., Barron, M. R., Hou, L., Soerens, A. G., Yu, J., et al. (2012). Extracellular matrix promotes highly efficient cardiac differentiation of human pluripotent stem cells: The matrix sandwich method. Circ. Res. 111, 1125-1136.

Although the foregoing subject matter has been described in some detail by way of illustration and example for purposes of clarity of understanding, it will be understood by those skilled in the art that certain changes and modifications can be practiced within the scope of the appended claims

That which is claimed:

1. A method for evaluating the cardiac effect of a compound, the method comprising:

(a) contacting a plurality of samples comprising one or more cardiac cells with the compound;

(b) pacing the one or more cardiac cells in each of the plurality of samples at two or more fixed rates;

(c) measuring pace-capture of the one or more cardiac cells in each of the plurality of samples in response to the compound at each of the two or more fixed rates; and (d) generating a single, color-coded visual representation that indicates a fraction of the plurality of samples that contain cardiac cells with extra beats compared to paced beats at each of the two or more fixed rates, and a fraction of the plurality of samples that contain cardiac cells with lost beats compared to paced beats at each of the two or more fixed rates.

2. The method of claim 1, wherein the color coded visual representation further indicates a fraction of the plurality of samples that contain cardiac cells that do not have extra beats or lost beats compared to paced beats at each of the two or more fixed rates.

3. The method of claim 1, wherein the method further comprises measuring a spontaneous response of the one or more cardiac cells in each of the plurality of samples to the compound prior to pacing the one or more cardiac cells at the two or more fixed rates.

4. The method of claim 3, wherein measuring the spontaneous response of the one or more cardiac cells comprises measuring one or more of pace-capture, repolarization time, contraction strength, and conduction velocity.

5. The method of claim 4, wherein the method further comprises reporting the measured spontaneous response of the one or more cardiac cells on a binary classification scale.

6. The method of claim 5, wherein the reported spontaneous response of each sample is compiled into a single visual representation.

7. The method of claim 6, wherein the visual representation is color coded.

8. The method of claim 1, wherein the two or more fixed rates have a range from about 0.5 Hz to about 2 Hz.

9. The method of claim 1, comprising pacing the one or more cardiac cells at three fixed rates.

10. The method of claim 1, comprising pacing the one or more cardiac cells at four fixed rates.

11. The method of claim 1, comprising pacing the one or more cardiac cells at five fixed rates.

12. The method of claim 1, further comprising measuring one or more of repolarization time, contraction strength, and conduction velocity of the one or more cardiac cells in each of the plurality of samples.

13. The method of claim 1, wherein each sample comprises a single cell, a cell monolayer, a cell cluster, engineered cardiac tissue, cardiac organoid, cardiac tissue explant, or whole heart.

* * * * *